United States Patent
Kessler et al.

(10) Patent No.: US 11,452,791 B2
(45) Date of Patent: Sep. 27, 2022

(54) FRAGRANCING AND/OR DEODORIZING A CLEANING APPLIANCE

(71) Applicant: Henkel AG & Co. KGaA, Duesseldorf (DE)

(72) Inventors: Arnd Kessler, Monheim am Rhein (DE); Thomas Weber, Weimar (DE); Johannes Zipfel, Amsterdam (NL); Christian Nitsch, Duesseldorf (DE); Lars Zuechner, Langenfeld (DE); Nadine Franke, Cologne (DE); Georg Wawer, Vienna (AT); Alexander Mueller, Monheim (DE); Wolfgang Wick, Dormagen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 435 days.

(21) Appl. No.: 16/468,831

(22) PCT Filed: Dec. 7, 2017

(86) PCT No.: PCT/EP2017/081859
§ 371 (c)(1),
(2) Date: Jun. 12, 2019

(87) PCT Pub. No.: WO2018/114364
PCT Pub. Date: Jun. 28, 2018

(65) Prior Publication Data
US 2020/0069834 A1    Mar. 5, 2020

(30) Foreign Application Priority Data
Dec. 21, 2016   (DE) ...................... 10 2016 225 838.9

(51) Int. Cl.
A61L 9/14      (2006.01)
A47L 15/42    (2006.01)
(Continued)

(52) U.S. Cl.
CPC ............. *A61L 9/14* (2013.01); *A47L 15/4276* (2013.01); *A61L 9/12* (2013.01);
(Continued)

(58) Field of Classification Search
CPC ........ A61L 9/14; A61L 9/12; A61L 2209/111; A61L 2209/13; A61L 2209/133;
(Continued)

(56) References Cited

U.S. PATENT DOCUMENTS 7,793,860 B2   9/2010 Bankers et al.
9,028,615 B2   5/2015 Eglmeier et al.
(Continued)

FOREIGN PATENT DOCUMENTS

CN       101111185 A      1/2008
DE   102007015246 A1 *  10/2008 ............. D06F 34/18
(Continued)

OTHER PUBLICATIONS

EPO, International Search Report and Written Opinion issued in International Application No. PCT/EP2017/081859, dated Mar. 13, 2018.

*Primary Examiner* — Sean E Conley
*Assistant Examiner* — Brendan A Hensel
(74) *Attorney, Agent, or Firm* — Lorenz & Kopf, LLP

(57) ABSTRACT

A method for fragrancing and/or deodorizing a cleaning appliance is disclosed. The method involves capturing first information or obtaining captured first information indicative of an odor load in the interior of the cleaning appliance, producing fragrancing and/or deodorizing information based at least in part on the captured or obtained first information or outputting the captured first information in order to produce fragrancing and/or deodorizing information of this type, and initiating fragrancing and/or deodorization by employing at least one actuator for releasing a fragrancing (Continued)

and/or deodorizing agent based on the fragrancing and/or deodorizing information produced. A corresponding dosing device, a device for carrying out and/or controlling the method, and a system with one or more devices for carrying out and/or controlling the method are also disclosed.

12 Claims, 9 Drawing Sheets

(51) Int. Cl.
*A61L 9/12* (2006.01)
*H04W 88/02* (2009.01)

(52) U.S. Cl.
CPC ...... *A61L 2209/111* (2013.01); *A61L 2209/13* (2013.01); *A61L 2209/133* (2013.01); *A61L 2209/135* (2013.01); *H04W 88/02* (2013.01)

(58) Field of Classification Search
CPC ........... A61L 2209/135; A47L 15/4276; A47L 2501/07; A47L 2401/34; A47L 15/4481; A47L 15/0021; A47L 2301/04; A47L 2401/03; A47L 2401/12; A47L 2401/30; A47L 2501/34; H04W 88/02
See application file for complete search history.

(56) References Cited

U.S. PATENT DOCUMENTS

| | | |
|---|---|---|
| 2005/0196046 A1 | 9/2005 | Hudnut et al. |
| 2008/0159907 A1 | 7/2008 | Joshi et al. |
| 2010/0139366 A1* | 6/2010 | Krausch ................ D06F 34/14 |
| | | 73/23.34 |
| 2011/0146716 A1 | 6/2011 | Deweerd et al. |
| 2011/0226808 A1 | 9/2011 | Lonski |
| 2014/0236328 A1 | 8/2014 | Kamon et al. |
| 2016/0091470 A1 | 3/2016 | Gafsou |
| 2016/0218884 A1 | 7/2016 | Ebrom et al. |
| 2018/0036448 A1* | 2/2018 | Becker ................... A61L 9/032 |

FOREIGN PATENT DOCUMENTS

| | | |
|---|---|---|
| DE | 102007015246 A1 | 10/2008 |
| DE | 102008025205 A1 | 12/2009 |
| DE | 102008054462 A1 | 6/2010 |
| DE | 102009026712 A1 | 12/2010 |
| EP | 1843693 B1 | 3/2014 |
| ES | 2574566 A1 | 6/2016 |
| KR | 20040000101 A | 1/2004 |
| KR | 20100022695 A | 3/2010 |
| WO | 2008119607 A1 | 10/2008 |

* cited by examiner

FRAGRANCING AND/OR DEODORIZING A CLEANING APPLIANCE

CROSS-REFERENCE TO RELATED APPLICATION

This application is a U.S. National-Stage entry under 35 U.S.C. § 371 based on International Application No. PCT/EP2017/081859, filed Dec. 7, 2017, which was published under PCT Article 21(2) and which claims priority to German Application No. 10 2016 225 838.9, filed Dec. 21, 2016, which are all hereby incorporated in their entirety by reference.

TECHNICAL FIELD

Exemplary embodiments relate to fragrancing and/or deodorizing a cleaning appliance, in particular fragrancing and/or deodorizing the interior of a cleaning appliance.

BACKGROUND

A known problem with cleaning appliances such as dishwashers is that, depending on the dirtiness (for example dirty crockery) and the length of time it is left, unpleasant odors can develop. The unpleasant odor is only dissipated when a cleaning program for the dishwasher is started. Often, for example for energy consumption reasons, a cleaning program for a dishwasher is only started when the space in the dishwasher for crockery to be cleaned is almost completely used up.

In order to alleviate the odor load or to cover it, fragrancing agents for dishwashers are known. As a rule, these fragrancing agents comprise support materials and aromatic substances on these support materials which are continuously dispensed into the environment.

The problem with this known solution is that the quantity of fragrancing agent which is dispensed is constant and continuous, until the fragrancing agent is completely used up. The fragrancing is carried out entirely independently of the actual odor burden. Accordingly, it is not possible to match it to the actual odor load. Furthermore, certain unpleasant odors cannot be removed effectively by this type of fragrancing, because when a fragrancing agent is dispensed constantly, it is only possible to cover over the unpleasant odor.

SUMMARY

Thus, in the light of the prior art described above, the objective is to at least partially alleviate or avoid the described problems, i.e. in particular, to provide the opportunity to make it possible to remove the odor load in an appropriate manner as a function of the odor load which is present.

This objective is achieved by employing an exemplary method in accordance with a first aspect, which comprises the following:
  capturing first information or obtaining captured first information indicative of an odor load in the interior of a cleaning appliance, wherein the first information is captured from at least one odor sensor;
  producing fragrancing and/or deodorizing information based at least in part on the captured or obtained first information or outputting the captured first information in order to produce fragrancing and/or deodorizing information of this type;
  initiating fragrancing and/or deodorization by at least one actuator for fragrancing and/or deodorizing agent based on the fragrancing and/or deodorizing information produced.

In an exemplary embodiment of the first aspect, the method comprises obtaining the captured first information and producing the fragrancing and/or deodorizing information. In another exemplary embodiment of the first aspect, the method comprises capturing the first information and outputting the captured first information in order to produce the fragrancing and/or deodorizing information.

In accordance with a second exemplary aspect, a dosing device for positioning in the interior of a cleaning appliance is disclosed, wherein the dosing device comprises:
  at least one cartridge for storing at least one preparation of a fragrancing and/or deodorizing agent;
  a sensor unit comprising at least one odor sensor;
  a control unit wherein, by the control unit, fragrancing and/or deodorizing information based on the first information captured from the sensor unit can be produced;
  an actuator for initiating fragrancing and/or deodorization based on the fragrancing and/or deodorizing information produced, wherein at least one preparation of a fragrancing and/or deodorizing agent can be released;
  optionally, a communication interface.

In accordance with a third exemplary aspect, a device is disclosed which is configured to carry out and/or control the method in accordance with the first aspect or which comprises respective agents for carrying out and/or controlling the steps of the method in accordance with the first aspect. In this regard, either all of the steps of the method may be managed, or all of the steps of the method may be implemented, or one or more steps may be managed, and one or more steps may be implemented. One or more of the means may also be implemented and/or managed by the same unit. As an example, one or more of the means may be formed by one or more processors.

In accordance with a fourth exemplary aspect, a device is disclosed which comprises at least one processor and at least one memory which contains program code, wherein the memory and the program code are configured to allow a device, with the at least one processor (for example the device with the processor and the memory), to implement and/or manage at least the method in accordance with the first aspect. In this manner, either all of the steps of the method may be managed, or all of the steps of the method may be implemented, or one or more steps may be managed, and one or more steps may be implemented.

In accordance with a fifth exemplary aspect, a system is disclosed which comprises one or more devices which are configured to implement and/or control the method in accordance with the first aspect or means for implementing and/or managing the steps of the method in accordance with the first aspect. In this manner, preferably, at least one device (1, 2, 3, 50, 51) comprises a communication interface. In this manner, either all of the steps of the method may be managed, or all of the steps of the method may be implemented, or one or more steps may be managed, and one or more steps may be implemented.

In accordance with a sixth exemplary aspect, a computer program is disclosed which comprises program instructions which allow a processor to implement and/or control the method in accordance with the first aspect when the computer program runs on the processor. The term "processor" as used in this specification should be understood to mean, inter alia, control units, microprocessors, microcontrol units such as microcontrollers, digital signal processors (DSP), application-specific integrated circuits (ASICs) or field programmable gate arrays (FPGAs). In this regard, either all of the steps of the method may be managed, or all of the steps of the method may be implemented, or one or more steps be managed, and one or more steps may be implemented. As an example, the computer program may be capable of being distributed over a network such as the interne, a telephone or cellular network and/or a local network. The computer program may be at least part of the software and/or firmware of a processor. At the same time, it may at least in part be implemented as hardware. The computer program may, for example, be stored on a computer-readable storage medium, for example a magnetic, electrical, electromagnetic, optical and/or other type of storage medium. The storage medium may, for example, be part of the processor, for example a (non-volatile or volatile) program memory of the processor, or a part thereof. The storage medium is, for example, physical, i.e. tangible, and/or non-transient.

These six aspects comprise, inter alia, the properties described below—occasionally by way of example.

The term "fragrancing" should be understood to mean a noticeable release of fragrancing substances. The fragrancing substances can be perceived by human olfactory receptors and translated by the brain into a fragrance. Fragrancing substances are active substances which are formed in animals or plants or are manufactured synthetically. For a substance to be perceivable as an odor, the substance has to be volatile. The volatility is a function of molecular size and the interaction with other molecules. The limit of volatility is reached at about a molecular mass of approximately 300 g/mol (this corresponds to approximately 20 carbon atoms). Aromatic substances which contain in the region of 8 to 16 carbon atoms are pleasant to humans.

The term "deodorizing" should be understood to mean a suitable measure for removing a disruptive bad odor. This may, for example, be carried out by physical means (for example by adsorption/absorption) or by chemical, non-reactive means. These chemical non-reactive means are capable of blocking out or masking a disruptive bad odor or of covering it with its own odor. However, for deodorizing, it is not vital to produce an "active" odor action.

An example of a cleaning appliance is a dishwasher.

First information is captured. Alternatively, captured first information is obtained. The first information is an indication of an odor load in the interior of a cleaning appliance. The first information thus, for example, provides a quantitative and/or qualitative measure of an odor load in the interior of a cleaning appliance.

The first information is captured with at least one odor sensor. The at least one odor sensor is, for example, a nitrogen-sensitive sensor. The presence of an amine may be detected by employing the at least one odor sensor, for example. The at least one odor sensor is, for example, an electrochemical sensor. The presence of ethanol may be detected by employing the at least one odor sensor, for example. The at least one odor sensor detects the presence of ethanol in the environment of the at least one odor sensor and produces an electrical corresponding to the concentration of the ethanol.

The presence of ethanol which, for example, can be detected by the at least one odor sensor, is an indication of microbial contamination. As an example, yeasts produce ethanol as a product of metabolization. At least one odor sensor which is configured as an electrochemical sensor—hereinafter also termed an ethanol sensor—has, for example, a variable response sensitivity which depends on an ethanol concentration in the gas phase. In this regard, the term dA/dT (which is represented by the electrical signal produced of the "current vs time curve"; the derivative of the current [ampere] with respect to time [T]) drops to smaller values with decreasing ethanol concentration. Correspondingly, the current vs time curve varies to flatter increases per unit time. Conclusions may, for example, be drawn from this regarding the absolute concentration present, and also a variation of concentration with time can be observed. A variation of concentration with time of this type occurs in particular with microbial contamination caused by microbial colonization. In this regard, the detection of the ethanol concentration by employing the at least one odor sensor in the interior of the cleaning appliance (in particular between two cleaning cycles of the cleaning appliance) is a particular indication of a microbial load or for the odor load in the interior of the cleaning appliance.

Surprisingly, it has been observed that by using at least one odor sensor which is configured as an ethanol sensor, in addition to the presence of ethanol, other alcohols, esters, ketones and aldehydes may be detected. In this regard, the electric signal produced by the at least one odor sensor varies accordingly.

By employing the first information captured by the at least one odor sensor, fragrancing and/or deodorizing information may be produced which enables the olfactory status of the interior of a cleaning appliance to be evaluated. In addition to the detectability of the presence and concentration of ethanol, in a multi-dimensional manner, the presence of a wide variety of fragrancing substances and bad odors may be detected. In this regard, only the sensitivity of the at least one odor sensor (in particular an ethanol sensor) is limited, depending on the substance. In the case in which the at least one odor sensor is configured as an ethanol sensor, a sensitivity classification between organic groups may be defined as follows, for example:

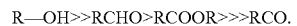

R—OH>>RCHO>RCOOR>>>RCO.

As an example, alcohols are detected significantly better than aldehydes. In turn, aldehydes are detected better than esters. Esters are detected significantly better than ketones.

When the method in accordance with the first aspect comprises obtaining captured first information, the captured first information is, for example, captured as described above.

Fragrancing and/or deodorizing information is produced which is at least partially based on the captured or obtained first information. The fragrancing and/or deodorizing information comprises, for example, a quantity, a frequency, a time, or a combination thereof. The initiation of fragrancing and/or deodorization of the interior of the cleaning appliance may be carried out based on the above values, for example.

Particularly having regard to the fact that as a rule, in the interior of a cleaning appliance, odor loads arise from a wide variety of foodstuffs, then a mixture of substances is present in the gas phase. The odor load emanating from the mixture of substances is, for example, captured by employing an at least one odor sensor. Because the odor loads are caused by a wide variety of foodstuffs, in an exemplary embodiment, the production of the fragrancing and/or deodorizing information comprises a comparison between the captured first information with a predefined threshold.

As an example, the predefined threshold is defined as the lowest sensitivity setting for the at least one odor sensor. A comparison between the captured first information and the predefined threshold is carried out. If the captured first information exceeds the predefined threshold, then, for example, fragrancing and/or deodorizing information is produced. The fragrancing and/or deodorizing information in this regard is, for example, an indication of an olfactory variation in the interior of the cleaning appliance. The olfactory variation may, for example, still be below a perception threshold for a person, because the odor load associated with the olfactory variation in the interior of the cleaning appliance is below an individual threshold of sensitivity. Accordingly, the fragrancing and/or deodorizing information may only comprise a small quantity as the indication of quantity, so that for small values of the first information captured by the at least one odor sensor, a small quantity of fragrancing and/or deodorizing agent can be released upon initiation of the fragrancing and/or deodorization. For larger and/or increasing variations in the values which are captured by the at least one odor sensor, the indication of quantity which is comprised in the fragrancing and/or deodorizing information may lead to an increase (automatic, for example) in the quantity of fragrancing and/or deodorizing agent to be released, or to a larger quantity. Alternatively, frequency information may be included in the fragrancing and/or deodorizing information which, in the context of initiating the fragrancing and/or deodorizing, repeatedly releases a small quantity of fragrancing and/or deodorizing agent (for example at intervals of time).

In accordance with an exemplary embodiment for all aspects, the captured first information and/or the predefined threshold are indicative of at least one of the following parameters:
  intensity of the odor load in the interior of the cleaning appliance;
  type of odor load in the interior of the cleaning appliance;
  dynamics of the odor load in the interior of the cleaning appliance;
  or a combination thereof.

The term "intensity of the odor load in the interior of the cleaning appliance" should in particular be understood to mean the odor load received by the user, which is represented by the amplitude of the electric signal produced by the at least one odor sensor. The greater the intensity of the odor load, the more rapid and more clearly can a user detect the odor load.

The term "type of odor load in the interior of the cleaning appliance" should in particular be understood to mean that of which the odor caused by the odor load primarily smells, i.e. which dimension of the odor is present. As an example, the type of odor load may include a qualitative statement, for example the odor load is of the "sour milk" or "vinegar" type, to cite some examples.

The term "dynamics of the odor load in the interior of the cleaning appliance" should in particular be understood to mean how quickly the intensity of an odor load increases over a period of time.

In accordance with an exemplary embodiment for all aspects, the method comprises:
  obtaining a user input concerning an adjustment of the predefined threshold;
  adapting the predefined threshold based on the obtained user input.

Capturing the user input comprises, for example, mechanically capturing information, for example an input on an input device which is carried out by the user, for example by employing keying in on a keypad and/or on a touch-sensitive display device. Acquisition of the user input may, for example take place using means for capturing the user input. When the user input is obtained, the user input obtained has been captured, for example as described above.

In accordance with an exemplary embodiment for all aspects, the method comprises:
  capturing second information or obtaining captured second information indicative of an ingress of light and/or a temperature in the interior of the cleaning appliance, wherein the second information is captured by at least one light sensor and/or at least one temperature sensor.

As an example, the at least one light sensor detects the ingress of light into the interior of the cleaning appliance which, for example, is caused by loading the cleaning appliance when the door of the cleaning appliance is opened. As a rule, the door of the cleaning appliance is closed again after a loading procedure. The time it is open and the variation in the amount of light ingress which can be captured by the at least one light sensor and, for example, caused by pulling out and pushing in the baskets provided to hold the crockery to be cleaned and putting in the crockery while the door of the cleaning appliance is open, can be an indication of the quantity of crockery which is put into the interior of the cleaning appliance while loading it. If after loading, the at least one cleaning sensor detects a variation as regards an odor load in the interior of the cleaning appliance, then appropriate fragrancing and/or deodorizing information is produced and an initiation of fragrancing and/or deodorization occurs. Correspondingly, the development of an odor load, which in particular can be perceived by a person, can be minimized or prevented. In an exemplary embodiment, the initiation of fragrancing and/or deodorization during loading of the cleaning appliance, i.e. while a door of the cleaning appliance is open, is prevented. Loading of the cleaning appliance can be determined, for example, via the second information captured by the at least one light sensor.

The at least one temperature sensor is, for example, at least one sensor which is suitable for capturing a temperature.

In accordance with an exemplary embodiment for all aspects, the method comprises:
  adapting the predefined threshold based on the captured second information, in particular adapting the predefined threshold by employing a zero-point calibration in the case in which the temperature has dropped below a predefined temperature threshold and the ingress of light has signaled emptying of the cleaning appliance.

In particular, calibration of the at least one odor sensor is made possible by the adaptation. During calibration, for example, the predefined threshold for comparison with the captured first information is established. What is known as a zero-point calibration may, for example, be carried out when the cleaning appliance is empty or clean and in particular can be commenced or triggered (automatically) when the empty or clean status of the cleaning appliance is detected, for example by an appropriate control signal from the processor.

In order to detect whether the cleaning appliance is empty or clean, firstly, a check is carried out as to whether the temperature in the interior of the cleaning appliance is below a predefined temperature threshold. Because when a cleaning cycle of the cleaning appliance is carried out, the prevailing temperature in the interior of the cleaning appliance is usually raised, then in the case in which the temperature according to the captured second information is above the predefined temperature threshold, then the cleaning appliance is not empty or clean.

In the case in which the temperature is below the predefined threshold, then, for example, an additional check is carried out as to whether any ingress of light has been detected (for example by at least one light sensor). Ingress of light in combination with a drop in temperature which, for example, can be captured via at least one temperature sensor, can indicate that emptying (for example of crockery) of the cleaning appliance has taken place. In the case that no ingress of light has been detected and correspondingly no emptied cleaning appliance has been signaled, then correspondingly, the cleaning appliance is not empty or clean.

When the temperature in the interior of the cleaning appliance drops below a specific temperature threshold and the cleaning appliance has been emptied, adaptation of the predefined threshold is carried out, for example, so that, for example, a zero-point calibration is carried out. In this regard, the first information captured by the at least one odor sensor (for example absolute measured values captured by the at least one odor sensor) is stored. This stored first information serves to monitor the ageing of the at least one odor sensor. The assessment of this stored first information may, for example be used in order to inform a user of the cleaning appliance when the sensitivity of the at least one odor sensor diminishes, and it should possibly be replaced in order to be able to ensure correct operation of the (automated) fragrancing and/or deodorizing.

The first information captured by the at least one odor sensor (for example absolute measured values captured by the at least one odor sensor), which is stored in the empty or clean state of the cleaning appliance, exemplifies a status of the interior of the cleaning appliance which is almost free from disruptive odors, i.e. a neutral odor load in the interior of the cleaning appliance. In order to check whether a neutral odor load exists in the interior of the cleaning appliance, initiating the release of a specific quantity of fragrancing and/or deodorizing agent may be carried out. In this regard, it must be ensured that at least one of the released fragrancing and/or deodorizing agents leads to a full signal deflection (100%) of the at least one odor sensor, but not to oversaturation. In the case in which the at least one odor sensor is configured as an ethanol sensor, then ethanol or a similarly acting alcohol may be released as the fragrancing and/or deodorizing agent. If this is not possible, then alternatively, for example, a calibration substance or an appropriate mixture which is stored separately (for example in the dosing device) can be introduced into the interior of the cleaning appliance, or alternatively, the calibration substance or the appropriate mixture may be introduced from outside.

If no full signal deflection (100%) is captured by the at least one odor sensor, an appropriate adaptation of the threshold may be undertaken so that, despite the function of the at least one odor sensor being compromised by ageing, it is still possible to detect an odor load in the interior of the cleaning appliance using the at least one odor sensor.

Alternatively or in addition, the predefined threshold may be manually adapted by a user. As an example, by adapting the predefined threshold, the user may set a maximum tolerable unpleasant odor load. Furthermore, the user may, for example, make a (manual) adjustment of the amount of fragrancing and/or deodorizing agent released when initiating fragrancing and/or deodorization, for example by employing, a quantity threshold. The quantity threshold may, for example, be included as a factor measured in the fragrancing and/or deodorizing information produced. As an example, the user may wish for reinforced fragrancing and/or deodorizing when the user is highly sensitive to an unpleasant odor load, for example. In particular, an adjustment of the quantity threshold may be reasonable when the unpleasant odor load in the interior of the cleaning appliance is caused by substances which, for example, cannot be detected by the at least one odor sensor.

In an exemplary embodiment for all aspects, the at least one odor sensor and the at least one light sensor and/or the at least one temperature sensor form a sensor array.

The sensor array comprises at least one odor sensor and at least one light sensor, for example. Alternatively or in addition, the sensor array comprises at least one temperature sensor. The sensor array comprises a plurality of odor sensors and a light sensor, for example. The sensor array comprises, for example, a plurality of individual sensors or a further sensor array, on which, in turn, various sensors may be disposed. The respective sensors may be configured as modules, so that they can be replaced on the sensor array, for example as a plug-in module. Alternatively or in addition, the sensor array may be replaceable, i.e. the sensor array is configured as a replaceable module. In particular, the sensor array comprises a plurality of sensors, by which the widest variety of organic groups can be detected such as, for example, alcohols, ketones, thiols, mercaptans, amines, esters, hydrocarbons or a combination thereof.

In accordance with an exemplary embodiment for all aspects, the method is carried out and/or controlled between two cleaning cycles of the cleaning appliance.

In accordance with an exemplary embodiment for all aspects, initiation of fragrancing and/or deodorization is carried out when the fragrancing and/or deodorizing information produced is indicative of an odor load in the interior of the cleaning appliance which is perceived by the user as unpleasant. In this regard, for example, the predefined threshold may be adapted accordingly, for example by employing a user input which in particular is indicative of the individual user sensitivities as regards an (odor) threshold that is perceived by the user as unpleasant. Odor impressions are highly subjective and complex perceptions and are perceived by people in very different manners. Thus, in this regard, it is particularly effective to work with cognitive, self-learning and/or adaptive methods in order to describe and evaluate the plurality of hedonic dimensions of odor, and finally to be able to offer the individual user a solution which is tailored to that individual.

In an exemplary embodiment for all aspects, initiation of fragrancing and/or deodorization releases different fragrancing and/or deodorizing agents, in particular as a function of the type of odor load in the interior of the cleaning appliance. Fragrancing and/or deodorization may be carried out in correspondence to the (for example captured and/or determined) type of the odor load in the interior of the cleaning appliance. An opportunity to describe the type of odor load arises, for example, from what is known as a Kohonen map. A Kohonen map of this type, for example from Mamlouk et al. from 2003, constitutes 32 odor dimensions. The odor dimensions describe an olfactory space in abstract terms such as, for example "fishy" or "plastic", behind which are concealed a plurality of substances which each cause this odor dimension. If, for example, an odor sensor detects an amine, then with the aid of a Kohonen map of this type, the electrical signal produced by the odor sensor can be translated into an odor description. The suitable fragrancing and/or deodorizing agent can be selected using the odor dimension. Alternatively or in addition, by employing the odor dimension, a Kohonen map can establish whether an odor load is or is not present. When a substance is detected by employing the odor sensor which falls into the olfactory category of bad odor (in contrast to odor dimensions which do not fall into the olfactory category of bad odor), this may be used to initiate appropriate fragrancing and/or deodorization.

In accordance with an exemplary embodiment for all aspects, initiation of fragrancing and/or deodorization releases different fragrancing and/or deodorizing agents, in particular as a function of the type of odor load in the interior of the cleaning appliance. Alternatively or in addition, initiation of fragrancing and/or deodorization releases different quantities of the fragrancing and/or deodorizing agent, in particular as a function of the intensity of the odor load in the interior of the cleaning appliance.

In an exemplary embodiment for all aspects, the fragrancing and/or deodorizing agent or the fragrancing and/or deodorizing agents are formulated and/or configured in a manner such that the at least one odor sensor cannot detect the fragrancing and/or deodorizing agent or the fragrancing and/or deodorizing agents. The fragrancing and/or deodorizing agent or the fragrancing and/or deodorizing agents correspondingly comprise or contain no substances to which the at least one odor sensor reacts. In this case the at least one odor sensor is thus "blind" to the fragrancing and/or deodorizing agent or the fragrancing and/or deodorizing agents. Correspondingly, the at least one odor sensor may exclusively detect substances or an odor load which are caused by an odor load in the interior of the cleaning appliance (for example by dirty crockery). In the context of producing fragrancing and/or deodorizing information, correspondingly, fragrancing and/or deodorizing agents that have already been released do not have to be taken into consideration. In this case, in order to adapt the predefined threshold, for example in the context of the zero-point calibration, a calibration agent which has to be stored separately from the fragrancing and/or deodorizing agent is necessary, or it has to be supplied from the outside (for example, manually by a user).

In a second aspect, the objective is achieved and embodied in an exemplary dosing device for positioning in the interior of a cleaning appliance, the dosing device comprising:
- at least one cartridge for storing at least one preparation of a fragrancing and/or deodorizing agent;
- a sensor unit comprising at least one odor sensor;
- a control unit wherein, by employing the control unit, fragrancing and/or deodorizing information based on the first information captured from the sensor unit can be produced;
- an actuator for initiating fragrancing and/or deodorization based on the fragrancing and/or deodorizing information produced, wherein at least one preparation of a fragrancing and/or deodorizing agent can be released;
- optionally, a communication interface.

In an exemplary embodiment in accordance with all aspects, the sensor unit comprises at least one light sensor and/or at least one temperature sensor. The sensor unit comprises at least one odor sensor and at least one light sensor, for example. Alternatively or in addition, the sensor unit comprises at least one temperature sensor. As an example, the sensor unit comprises a plurality of odor sensors and a light sensor. As an example, the sensor unit comprises a plurality of individual sensors or a sensor array, on which various sensors can be disposed. The respective sensors may be modular in configuration, so that they can be replaced on the sensor unit, for example as a plug-in module. Alternatively or in addition, the sensor array may be replaceable, for example; as an example, the sensor array is configured as a replaceable module. In particular, the sensor unit comprises a plurality of sensors, by which the most widely different organic groups can be detected, such as, for example, alcohols, ketones, thiols, mercaptans, amines, esters, hydrocarbons, or a combination thereof.

The dosing device comprises the control unit, sensor unit as well as, optionally, at least one energy source necessary for operation. In a further embodiment, the dosing device comprises at least one actuator which is connected to the energy source and the control unit in a manner such that a control signal from the control unit causes movement of the actuator.

In an exemplary embodiment, the dosing device may be formed from a spray-protected housing which prevents spray that may, for example, be produced when a dishwasher is in use, from penetrating, into the interior of the dosing device.

In an exemplary embodiment, the energy source, the control unit as well as the sensor unit in particular are molded in a manner such that the dosing device is essentially watertight, and the dosing device is thus also capable of functioning even when completely surrounded by liquid. Examples of molding materials that may be used are multi-component epoxy and acrylate molding masses such as methacrylate esters, urethane methacrylate and cyanacrylate, or two-component materials with polyurethanes, silicones, or epoxy resins.

An alternative or supplement to molding is constituted by encapsulation of the components in an appropriately constructed, moisture-proof housing. An embodiment of this type will be described in more detail below.

In an exemplary embodiment, the dosing device comprises at least one first interface which cooperates with a corresponding interface in or on a water-bearing appliance such as, in particular, a water-bearing household appliance, preferably a dishwasher, in a manner such that electrical energy can be transferred from the water-bearing appliance to the dosing device.

In one embodiment, the at least one interface is formed by plug-in connectors. In a further embodiment, the at least one interface may be configured in a manner such that a wireless transfer of electrical energy is possible, for example by induction.

In this regard, particularly preferably, the interfaces are inductive transmitters or receivers of electromagnetic waves. In this manner, in particular, the interfaces of a water-bearing appliance such as a dishwasher, for example, may be configured as a transmitter coil with an iron core operated by alternating current and the interface of the dosing device may be configured as a receiver coil with an iron core.

In one embodiment, the energy source may also be disposed in at least one cartridge. This means that the cartridge can be electrically coupled to the dosing device. Because the cartridge is going to be replaced anyway, preferably at intervals, then in this way, an energy supply for the dosing device is guaranteed.

In an exemplary further development, a respective second interface is provided on the dosing device and the water-bearing appliance, such as a dishwasher, in order to transmit electromagnetic signals which in particular represent operational status, measurement and/or management information from the dosing device and/or the water-bearing appliance such as a dishwasher.

In particular, an interface of this type may be configured in a manner such that a wireless transmission of electromagnetic signals is possible. The wireless transmission of data may, for example, be carried out by radio transmission or IR transmission.

The term "cartridge" as used in the context of this application should be understood to mean a packaging suitable for sheathing or holding together flowable or spreadable substances such as fragrancing and/or deodorizing agents and which, in order to dispense the substance, can preferably be coupled to a dosing device. The substance which can be accommodated in the cartridge is intended for repeated dosing. The dosing device preferably comprises at least two cartridges which can each be coupled to the dosing device. At least one, preferably each of the cartridges may be releasably coupled to the dosing device. In order to dispense fragrance and/or deodorant into a volume of from about 100 to about 200 L (for example in order to remove an unpleasant odor load in the interior of a cleaning appliance), only small quantities of active substances (for example fragrancing and/or deodorizing agents) are necessary, because many fragrancing substances such as, for example, fragrancing and/or deodorizing agents, have very low odor thresholds. Some examples of fragrancing and/or deodorizing agents and their odor thresholds in water are listed below:

Odor threshold in water:
Linalool: about 6 µg/mL
Citronellol: about 10 µg/mL
Beta-ionone: about 0.007 µg/mL
Beta-damascenone: about 0.002 µg/mL.

It can be seen from this that fragrancing and/or deodorizing agents can already be effective in small quantities. This also means that only small volumes of fragrancing and/or deodorizing agents have to be stored.

In an exemplary embodiment, the at least two cartridges may be configured with a plurality of mutually spatially separated chambers each for accommodating different substances of a fragrancing and/or deodorizing agent. In particular, a cartridge may comprise a plurality of chambers which can be filled with mutually different fragrancing and/or deodorizing agents. In this manner, a combined use of fragrancing and/or deodorizing agents is made possible.

In an exemplary embodiment, the cartridge comprises at least one outlet opening, which is configured in a manner such that a gravity-operated release of substance from the container in the position of use of the dosing device may be carried out. Because of this, no other propellants are required to release substances from the container, whereupon the construction of the dosing device is simple, and the manufacturing costs can be kept down.

In a further exemplary embodiment, at least one second chamber may be provided to accommodate at least one second flowable or spreadable substance, wherein the second chamber comprises at least one outlet opening, which is configured in a manner such that a gravity-operated release of product from the second chamber is carried out in the position of use of the dosing device. In particular, the provision of a second chamber is then advantageous when substances are stored in the mutually separated containers which cannot normally be stored together in a stable manner.

Furthermore, more than two, in particular three to four chambers may be provided in or on a cartridge. In particular, one of the chambers may be configured to dispense volatile substances such as an aromatic substance, for example, into the environment.

In a further exemplary embodiment, the cartridge may be configured as one piece. In this manner, the cartridge, in particular by using a suitable blow molding process, can be cost-effectively produced in a single manufacturing step. The chambers of the cartridge may in this regard be separated from each other by webs or bridges of material, for example.

The cartridge may also be formed in multiple pieces by components which are manufactured by injection molding and subsequently joined together. Furthermore, it is envisageable for the cartridge to be formed in multiple parts in a manner such that at least one chamber, preferably all of the chambers, can be individually removed from the dosing device or inserted into the dosing device. In this manner, if one substance is used to a different extent, it is possible to remove an already empty chamber while the remaining chambers, which could still be full of a substance, remain in the dosing device. In this manner, the individual chambers or their substances can be refilled in a focused and appropriate manner.

The chambers of a cartridge may be fixed together using suitable connection methods, so that a container unit is formed. The chambers may be fixed to each other releasably or non-releasably by suitable interlocking, force-fitting or material bonded connections. In particular, fixing may be carried out by one or more of the types of connection from the group formed by snap connections, hook-and-loop connections, press connections, fusion connections, bonded connections, welded connections, soldered connections, screw connections, wedge connections, clamp connections or snap-fit connections. In particular, fixing may also be carried out by employing a shrink sleeve which is pulled over the entirety of or sections of the cartridge while warm and which when cooled, securely encloses the chambers or the cartridge.

In order to provide the chambers with advantageous residual emptying properties, the base of the chambers may be inclined towards the dispensing opening in the shape of a funnel. Furthermore, the inner wall of a chamber may be configured by a suitable choice of material and/or configuration of the surface in a manner such that adhesion of substance to the inner wall of the chamber is low. This measure also means that the ability of a chamber to empty out residues is further optimized.

The chambers of a cartridge may have the same or different fill volumes. In a configuration with two chambers, the ratio of the container volume is preferably about 5:1; in a configuration with three chambers, it is preferably about 4:1:1, wherein these configurations are particularly suitable for use in dishwashers.

In or on a chamber, a dosing chamber may be provided upstream of the outlet opening in the direction of flow of the substance. By employing the dosing chamber, the quantity of substance which is to be dispensed from the chamber when the substance is released into the environment can be set. This is of particular advantage when the closure element of the dosing device, which acts to dispense the substance from a chamber into the environment, can dispense it all at once and then can be closed without controlling the dispensed quantity. The dosing chamber then ensures that a predefined quantity of substance is released without a direct feedback of the dispensed substance quantity. The dosing chambers may be formed as one piece or in multiple pieces.

In accordance with a further exemplary development, one or more chambers adjacent to an outlet opening may each be provided with a liquid-tight closable chamber opening. As an example, it is then possible to refill substances stored in this chamber through this chamber opening.

In order to ventilate the chambers, ventilation possibilities may be provided, in particular in the upper region of the chamber, in order to ensure pressure equilibration between the interior of the chambers and the environment as the level of the chambers falls. These ventilation possibilities may, for example, be configured as a valve, in particular a silicone valve, micro-openings in the chamber wall, or the like.

In accordance with a further embodiment, if the chamber is not directly ventilated, but rather via the dosing device or is not ventilated at all, for example when flexible containers are used such as bags, for example, then this has the advantage that under the raised temperatures during a wash cycle of a cleaning appliance, a pressure is built up by heating of the contents of the chamber, which forces the substances to be dosed in the direction of the outlet openings, meaning that good residual emptying capacity of the cartridge is obtainable. Furthermore, with packaging of this type, preferably vacuum packaging, there is no danger of oxidation of the substances. Whereupon bag packaging or even bag-in-bottle packaging can in particular be appropriately used for substances that are sensitive to oxidation.

The cartridge usually has a fill volume of <5000 mL, in particular <1000 mL, preferably <500 mL, particularly preferably <250 mL, more particularly preferably <50 mL.

The cartridge may have any shape. As an example, it may be configured in the shape of a cube, a sphere or it could be in the shape of a plate.

The cartridge and the dosing device may in particular have a spatial shape that is such that they ensure as little a loss of useful volume as possible, in particular in a dishwasher.

In an exemplary embodiment, at least one cartridge has a depletion indicator. It may be what is known as an end of life indication, which can indicate that the fragrancing and/or deodorizing agent accommodated in a cartridge or a chamber of a cartridge is exhausted or almost exhausted. In order to provide a direct optical check on the fill level, at least a section of the cartridge may be formed from a transparent material. Furthermore, an end of life signal may be produced by a residual quantity in the cartridge. In this regard, for example, because the volume of fragrancing and/or deodorizing agent accommodated in the cartridge is known and because the quantity that is dispensed per executed and/or managed dose of fragrancing and/or deodorizing agent is known, a calculation may be carried out so that the residual quantity of fragrancing and/or deodorizing agent inside the cartridge can be calculated.

In order to protect heat-sensitive components of a substance in a cartridge from the effects of heat, the cartridge may be manufactured from a material with a low heat conductivity.

A further possibility for alleviating the influence of heat on a substance in the cartridge is by insulating the cartridge using suitable means, for example by using heat insulating material such as expanded polystyrene, for example, which completely or partially surrounds the cartridge or a chamber of the cartridge in a suitable manner.

When a plurality of chambers is present, a further means for protecting heat-sensitive substances in a cartridge concerns the disposition thereof with respect to each other. Thus, for example, it may be envisaged that the chambers which contain a heat-sensitive product could be partially or completely enclosed by at least one further chamber filled with a substance, wherein, in this configuration, this substance and this chamber serve as heat insulation for the enclosed chamber. This means that a first chamber which contains a heat sensitive substance is partially or completely surrounded by at least one further chamber filled with a substance so that, when the environment heats up, the heat sensitive substance in the first chamber exhibits a slower temperature rise than the substance in the surrounding chambers.

In order to further improve the thermal insulation, when using more than two chambers, the chambers may be disposed around each other in the manner of Russian dolls, so that a multi-layered insulating layer is formed.

In particular, it is advantageous for at least one substance which is stored in a surrounding chamber to have a thermal conductivity of between about 0.01 and about 5 W/m.K, preferably between about 0.02 and about 2 W/m.K, particularly preferably between about 0.024 and about 1 W/m.K.

In particular, the cartridge may be configured so as to have a stable shape. However, it is also possible to envisage the cartridge as being configured as a flexible packaging means, for example as a tube. Furthermore, it is also possible to use flexible containers such as bags, in particular when they are used in accordance with the "bag in bottle" principle in a receiving container which is essentially stable in shape. By using a flexible packaging—in contrast to using the packaging described above, which are stable in shape (cartridge)—a ventilation system to equilibrate the pressure is no longer necessary.

In an exemplary embodiment, the cartridge may have a RFID label which at least contains information regarding the contents of the cartridge, and which can be read in a contactless manner by the sensor unit.

This information may, for example be used in order to select a dosing program stored in the control unit which, for example, initiates fragrancing and/or deodorization. In this manner, it can be ensured that an optimal dosing program is always used for a specific fragrancing and/or deodorizing agent. Furthermore, when a RFID label is not present or when a RFID label has an incorrect or defective identification, then it is possible not to dose via the dosing device, and instead to produce an optical or acoustic signal which advises the user of the problem.

In order to exclude misuse of a respective cartridge, the cartridges may also be provided with structural elements which cooperate with corresponding elements of the dosing device in accordance with the key and lock principle so that, for example, only cartridges of a specific type can be coupled to the dosing device. Furthermore, this embodiment means that it is possible for information regarding the cartridge coupled to the dosing device to be transmitted to the control unit.

The outlet openings of a cartridge may be disposed in a line, whereupon a slim, plate-shaped configuration of the dosing device is made possible.

In particular, the cartridge may, for example, be configured to accommodate (for example towable) fragrancing and/or deodorizing agents. Particularly preferably, a cartridge of this type comprises a plurality of chambers which can each accommodate different substances of a fragrancing and/or deodorizing agent.

The cartridge may comprise a cartridge floor which is directed vertically downwardly in the position of use and in which at least two chambers are provided, each with at least one outlet opening disposed at the cartridge floor.

Furthermore, the cartridge may be formed from at least two mutually material-bonded connected elements, wherein the connecting edges of the elements run on the cartridge floor outside the outlet openings, and thus the connecting edges do not intersect with the outlet openings.

The material-bonded connection may, for example, be produced by bonding, welding, soldering, pressing or vulcanization.

In an exemplary embodiment, the connecting edge runs along the head, floor and side faces of the cartridge. In this manner, two cartridge elements may in particular be manufactured using an injection molding process, wherein either both elements are formed in the shape of dishes or one element is in the shape of a dish and the second element is in the form of a cover.

In order to construct a two or multi-chamber cartridge, at least one of the two cartridge elements may comprise at least one separating web which, when the elements are joined together, respectively separates two adjacent chambers of the cartridge from each other.

As an alternative to forming one of the cartridges using two dish-shaped cartridge elements, it is also possible for one cartridge element to be a bowl-shaped container with at least one chamber and for the second element to be the cartridge floor or top, which is connected to the bowl-shaped container in a liquid-tight manner along the connecting edge.

Clearly, it is also possible for the cartridge configurations discussed above to be combined together in any suitable manner. As an example, it is possible to form a dual-chamber cartridge from a cartridge element in the form of a dish and a cartridge element in the form of a cover and to dispose a third one- or multi-part chamber on the top or lateral surface of the cartridge which is formed in this manner.

In particular, a further chamber of this type for accommodating a substance may be disposed on the respective cartridge and be configured in a manner such that volatile substances such as aromatic substances are dispensed into the environment of the chamber.

In accordance with an exemplary embodiment, the outlet openings may each be provided with a closure which, when coupled with a dosing device, allows a substance to flow out of the respective chamber and when uncoupled from the cartridge, essentially prevents substances from flowing out. In particular, the closure is configured as a silicone valve.

The cartridge elements forming the respective cartridge are preferably formed from a plastic and may be shaped in a common injection molding process, wherein it may be advantageous to form a connecting web between the two elements which acts as a hinge so that after unmolding, the two elements are folded over to lie next to each other and be material-bonded to each other along the connecting edge.

In a further embodiment, at least one energy source, in particular a battery or accumulator, may be disposed on one or more of the cartridges, preferably on the floor of a respective cartridge. Furthermore, features for electrically coupling the energy source with the dosing device may be provided on the cartridge.

The cartridge may be configured in a manner such that it can be releasably or fixedly disposed in or on the dosing device, for example inside the dishwasher. In an exemplary embodiment, each of a plurality of cartridges can be releasably or fixedly coupled to the dosing device. In this manner in particular, for example, exhausted, i.e. empty cartridges can be replaced, or cartridges wherein the substance accommodated in the cartridge has been completely or nearly completely consumed can be replaced. As an example, it is possible to replace each of the cartridges separately or individually. In this manner, only consumed substance such as fragrancing and/or deodorizing agent is replaced.

In the context of this application, a "control unit" may be a device which is suitable for influencing and/or implementing and/or controlling the transport of material, energy and/or information. The control unit in this regard influences an actuator, for example, with the aid of a control signal. A control signal may comprise information, in particular measurement signals, parameters or the like.

In an exemplary embodiment, through the control unit, dosing of a quantity of fragrancing and/or deodorizing agent which may be accommodated in a cartridge, for example, may be carried out. Carrying out an appropriate dosing function or dosing a quantity may, for example, be carried out by dispensing fragrancing and/or deodorizing, agent from the cartridge which can be coupled to the dosing device sequentially or simultaneously, continuously or discontinuously. Accordingly, dispensing of the fragrancing and/or deodorizing agent which may be accommodated in the cartridges can be activated or deactivated in order to carry out either continuous or discontinuous dispensing of the fragrancing and/or deodorizing agent. Furthermore, for example, a timely dosing function may be carried out, for example based on a control signal from the control unit. In this manner, for example, a substance can be dispensed through the dosing device between cleaning cycles or cleaning programs of a dishwasher. Based on a control signal, the fragrancing and/or deodorizing may be carried out essentially automatically and/or independently. As an example, a user does not need to input any information. Because of the information captured by the control unit from one or more devices for measuring and/or determining information, for example sensors, which will be described in more detail below, a control signal can be generated which enables or carries out an appropriate (i.e. based on the (first) information captured using the sensor unit) fragrancing and/or deodorization, or allows it to be carried out.

In an exemplary embodiment, a control signal from the control unit may initiate an action, in particular initiate fragrancing and/or deodorization of fragrancing and/or deodorizing agents. The action is, for example, to carry out or allow said fragrancing and/or deodorization. It is also possible for the control signal to take another action or to implement it. As an example, the control signal may be forwarded to a further device, for example an external device. Forwarding may, for example, be carried out via an appropriate interface for the transmission of information, in particular for forwarding the control signal. The control signal may, for example, be forwarded to a display device so that status information, for example, can be displayed, which in particular is displayed optically, acoustically and/or haptically. In this regard, for example, the dosing device may be monitored, controlled and/or managed "from outside". In addition, process information, identification data and/or measurement values captured by the sensor unit may be generated and transmitted to an external device. An external device may, for example, support an appropriate dose based on the control signal. As an example, it is possible to envisage reinforcing the action of a fragrancing and/or deodorizing agent, for example of a deodorizing substance by irradiating crockery with UV radiation, in particular UV-C radiation, which is initiated on the basis of the control signal. In the case of essentially automatic dosing of fragrancing and/or deodorizing agents, this makes dosing, in particular for a user, substantially easier, because no inputs, for example as regards control and/or regulation of the dosing device by the user, are necessary.

In particular, the control unit may be a programmable microprocessor. In an exemplary embodiment, a plurality of dosing programs is stored on the microprocessor, which can initiate dispensing of appropriate fragrancing and/or deodorizing agents that can be accommodated in the at least two cartridges.

In an exemplary embodiment, the control unit does not have any connection to any control system of the household appliance. This means that no information, in particular electrical and/or electromagnetic signals, is exchanged directly between the control unit and the control system of the household appliance.

In an alternative embodiment, the control unit may be coupled to the control system of the cleaning appliance. Preferably, this coupling is cableless. As an example, a signal may be transmitted wirelessly to the dosing device when the control system for the dishwasher actuates fragrancing and/or deodorization.

A plurality of programs for releasing different fragrancing and/or deodorizing agents may be stored in the control unit.

In an exemplary embodiment, the appropriate program may be called up by appropriate RFID labels or by physical information carriers formed on the container. In this manner, it is possible, for example, to use the same control unit for a plurality of applications, for example to initiate fragrancing and/or deodorizing.

In order to initiate fragrancing and/or deodorizing from fragrancing and/or deodorizing agents in particular for the purposes of regulation, the control unit may be configured in a manner such that on the one hand the fragrancing and/or deodorizing is carried out in a sufficiently short time period for ensuring a good result, and on the other hand, fragrancing and/or deodorization is not dosed so quickly that the surge becomes gelled. It may, for example, be carried out by carrying out the release at intervals, whereby the individual intervals may be set in a manner such that the correspondingly dosed quantity can be initiated entirely during one cycle, or that fragrancing and/or deodorization can be initiated.

In the context of this application, a "sensor" may be a device for measuring and/or determining information, for example a transducer or probe, which can capture physical or chemical properties and/or can capture the material quality of its environment qualitatively or quantitatively as a measured value.

In a further exemplary embodiment, the dosing device may be a device for capturing information, for example it may have a sensor which can determine physical, chemical and/or mechanical parameters from the environment of the dosing device. The sensor unit may comprise one or more active and/or passive sensors for the qualitative and/or quantitative acquisition of mechanical, electrical, physical and/or chemical parameters which are passed to the control unit as information.

An odor sensor may, for example, comprise one or more electrochemical sensors or be formed therefrom; they are capable of determining the presence of specific aromatic substances or bad odors. In particular, they may, for example, be sensors which can capture sulfur-containing aromatic substances, volatile carboxylic acids, volatile hydrocarbons and/or nitrogen-containing compounds. Examples of sensors of this type may have a surface with signal-generating binder molecules. These signal-generating binder molecules may be connected via a chemical and/or physical backbone to a signal transmitter such as, for example a quantum bit, a nanoparticle, a micelle, a vesicle or a membrane.

A data line between a device for measuring or determining information, for example the devices described above, and the control unit may be formed via an electrically conducting cable, or it may be cableless.

A cableless data line is in particular configured to transmit electromagnetic waves. Preferably, a cableless data line is configured in accordance with standards such as, for example, Bluetooth, IrDA, IEEE 802, Zigbee, NFC, etc.

In an exemplary embodiment, the sensor unit is disposed on the floor of the dosing device, wherein in the position of use, the floor of the dosing device is directed vertically downwardly.

In the context of this application, the "at least one energy source" should be understood to mean a constructional element of the dosing device which is appropriate for the provision of energy suitable for operating the dosing device. Preferably, the dosing device comprises at least one energy source and the at least one energy source is configured in a manner such that the dosing device is independent, in particular of an external energy source.

Preferably, the at least one energy source provides electrical energy. The energy source may, for example, be a battery, an accumulator, a power supply unit, a solar cell or the like.

In an exemplary embodiment, the energy source is replaceable, for example in the form of a replaceable battery.

A battery may, for example, be selected from the group formed by alkali-manganese batteries, zinc-carbon batteries, nickel-oxyhydroxide batteries, lithium batteries, lithium-iron sulfide batteries, zinc-air batteries, zinc chloride batteries, mercury-zinc batteries and/or silver oxide-zinc batteries.

Examples of suitable accumulators are lead accumulators (lead dioxide/lead), nickel-cadmium accumulators, nickel-metal hydride accumulators, lithium ion accumulators, lithium-polymer accumulators, alkali-manganese accumulators, silver-zinc accumulators, nickel-hydrogen accumulators, zinc-bromine accumulators, sodium-nickel chloride accumulators and/or nickel-iron accumulators.

In particular, the accumulator may be configured in a manner such that it can be recharged by induction.

However, it is also possible to use mechanical energy sources of one or more coil springs, torsion springs or torsion bars, spiral springs, air springs/gas springs and/or elastomeric springs.

The energy source is dimensioned in a manner such that the dosing device can carry out approximately 300 fragrancing and/or deodorizing cycles before the energy source is exhausted. Particularly preferably, the energy source can carry out between about 1 and about 300 cycles, more particularly preferably between about 10 and about 300, yet more preferably between about 100 and about 300 cycles before the energy source is exhausted.

Furthermore, features for transforming energy may be provided in or on the dosing device, which produce a voltage by features of which the accumulator is charged. As an example, these features may be configured as a dynamo which is operated by the flow of water during a washing operation in a dishwasher and thus pass the voltage produced to the accumulator.

In a further exemplary embodiment, the dosing device comprises at least one vibratory atomizer via which it is possible to transfer a fragrancing and/or deodorizing agent into the gas phase or to maintain it in the gas phase. Thus, for example, it may be envisaged that fragrancing and/or deodorizing agent could be vaporized, misted and/or sprayed by the vibratory atomizer, whereupon the fragrancing and/or deodorizing agent is transferred into the gas phase or forms an aerosol in the gas phase, wherein the gas phase is usually air.

This embodiment is particularly advantageous when used in a dishwasher in which a corresponding release of fragrancing and/or deodorizing agents into the gas phase is carried out in a closable rinsing or washing chamber. The fragrancing and/or deodorizing agent introduced into the gas phase can be uniformly distributed in the rinsing chamber and be condensed on the items to be washed in the dishwasher.

The fragrancing and/or deodorizing agent released through the vibratory atomizer may be selected from the group formed by surfactant-containing fragrancing and/or deodorizing agents, enzyme-containing fragrancing and/or deodorizing agents, odor-neutralizing fragrancing and/or deodorizing agents, biocidal fragrancing and/or deodorizing agents, or antibacterial fragrancing and/or deodorizing agents.

By applying the fragrancing and/or deodorizing agent to the items to be washed from the gas phase, a uniform layer of the corresponding fragrancing and/or deodorizing agent is applied to the surface of the items to be washed. Particularly preferably, the entirety of the surfaces of the items to be washed is wetted by the fragrancing and/or deodorizing agent.

In this manner, for example, action can be taken before the start of a cleaning program in a dishwasher which releases water. As an example, by employing a suitable fragrancing and/or deodorizing agent, the occurrence of bad odors due to biological decomposition processes of food residues stuck on the items to be washed can be suppressed.

Furthermore, after the end of the cleaning program of a dishwasher, a fragrancing and/or deodorizing agent may be applied to the items to be washed through the vibratory atomizer. In this regard, an antibacterially acting fragrancing and/or deodorizing agent or a fragrancing and/or deodorizing agent for modifying surfaces may be applied.

The physical objective is in particular achieved by employing the use of a dosing device inside a dishwasher.

In a further embodiment, at least one of the devices for carrying out one of the methods described below, which can be carried out with the dosing device and/or is manageable therefrom, is a mobile device. In particular, communication may be made via a communication system between a mobile device, for example a smart phone, laptop, tablet, wearable, computational engine and at least one other device, for example a server.

In accordance with an exemplary embodiment, the dosing device comprises a communication interface. As an example, the communication interface is set up for wired or wireless communication. As an example, the communication interface is a network interface. The communication interface is configured, for example, so as to be able to communicate with a communication system. Examples of a communication system are a local network (LAN), a wide area network (WAN), a wireless network (for example in accordance with the IEEE-802.11 standard, Bluetooth (LE) standard and/or the NFC standard), a wired network, a cellphone network, a telephone network and/or the internet. A communication system may comprise communication with an external computer, for example via an internet connection.

In accordance with an exemplary embodiment, the dosing device comprises at least one processor and at least one memory with computer program code, wherein the at least one memory and the computer program code are configured in a manner such that with the at least one processor, at least one method according to the aspects described below can be carried out and/or managed. The term "processor" should be understood to mean, for example, a control unit, a microprocessor, a microcontrol unit such as a microcontroller, a digital signal processor (DSP), an application-specific integrated circuit (ASIC) or a field programable gate array (FPGA).

As an example, an exemplary dosing device further comprises features for storing information such as a program memory and/or a central memory. As an example, an exemplary dosing device further comprises respective features for receiving and/or transmitting information via a network, such as a network interface.

An example of a dosing device is or comprises approximately one data processing unit, which is software-based and/or hardware-based, in order to be able to carry out the respective steps of an exemplary method in accordance with the aspects. Examples of a data processing unit are a computer, a desktop computer, a server, a thin client, a computational engine and/or a mobile computer (mobile device), such as a laptop computer, a tablet computer, a wearable, a personal digital assistant or a smartphone.

The exemplary embodiments described above in this description should also be understood to have been disclosed in all combinations. In particular, exemplary embodiments relating to the various aspects should be understood to have been disclosed.

In particular, the description above or below of steps of the method in accordance with preferred embodiments of a method also disclose corresponding means for carrying out the steps of the method using preferred embodiments of a device. Similarly, the disclosure of means in a device for carrying out a step of the method also discloses the corresponding step of the method.

Further advantageous exemplary embodiments can be discerned from the following detailed description of some exemplary embodiments, in particular in association with the figures. However, the figures serve solely for the purposes of illustration, and not for the determination of the scope of protection. The figures are not true to scale and solely illustrate the general concept by way of example. In particular, features which are contained in the figures should not in any way be assumed to be necessary components.

BRIEF DESCRIPTION OF THE DRAWINGS

The present disclosure will hereinafter be described in conjunction with the following drawing figures, wherein like numerals denote like elements, and.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Figure 1:
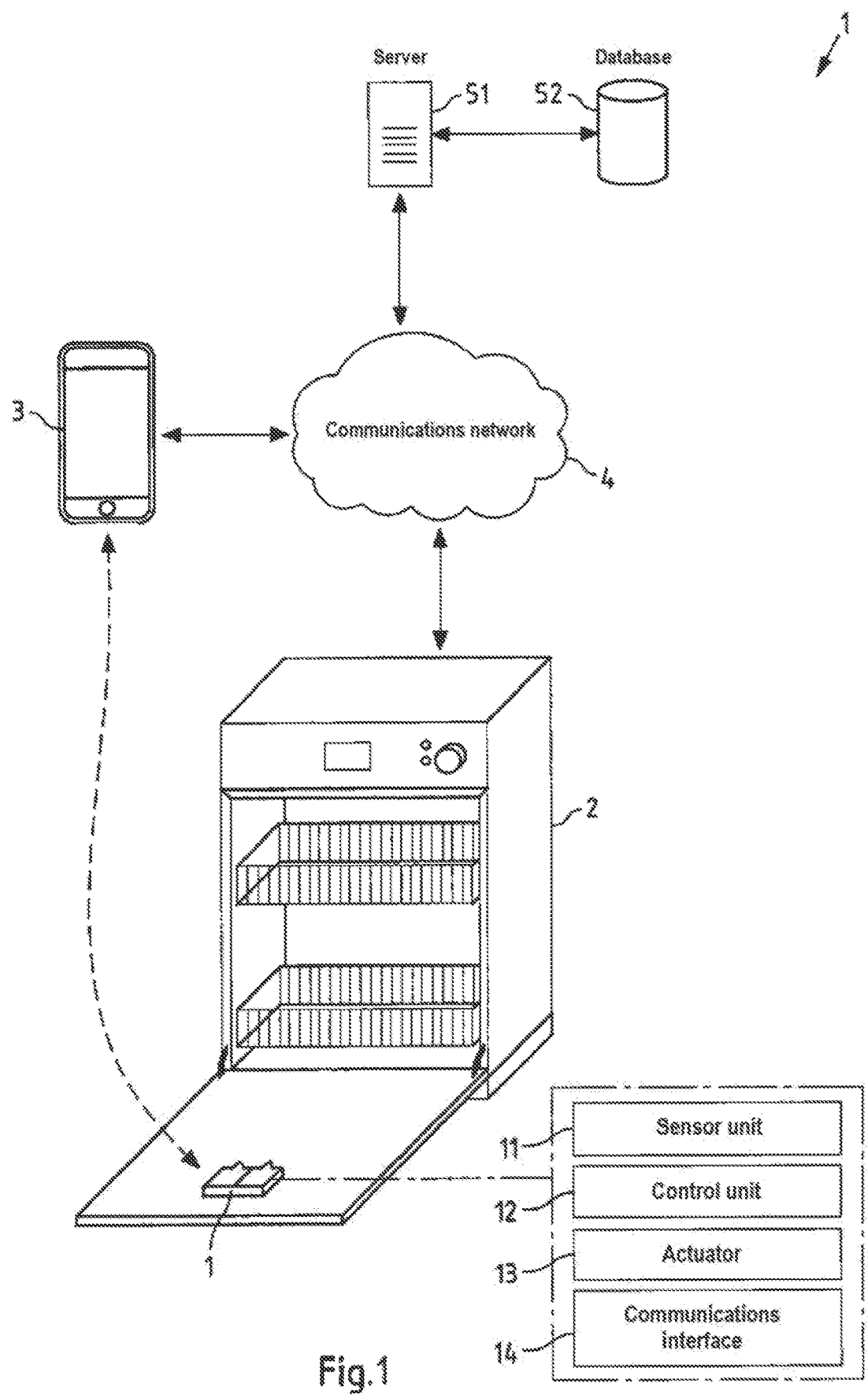
FIG. 1 shows a diagrammatic representation of an exemplary embodiment of a system in accordance with the fifth aspect.

FIG. 1 is a diagrammatic representation of an exemplary embodiment of a system 1. The system comprises a dosing device 1, a cleaning appliance 2 (for example a dishwasher), a mobile device 3 (for example a smart phone), a communication network 4 and a (centralized or decentralized) computing and storage device. The computing and storage device here comprises a server 51 and a database 52.

Figure 5:
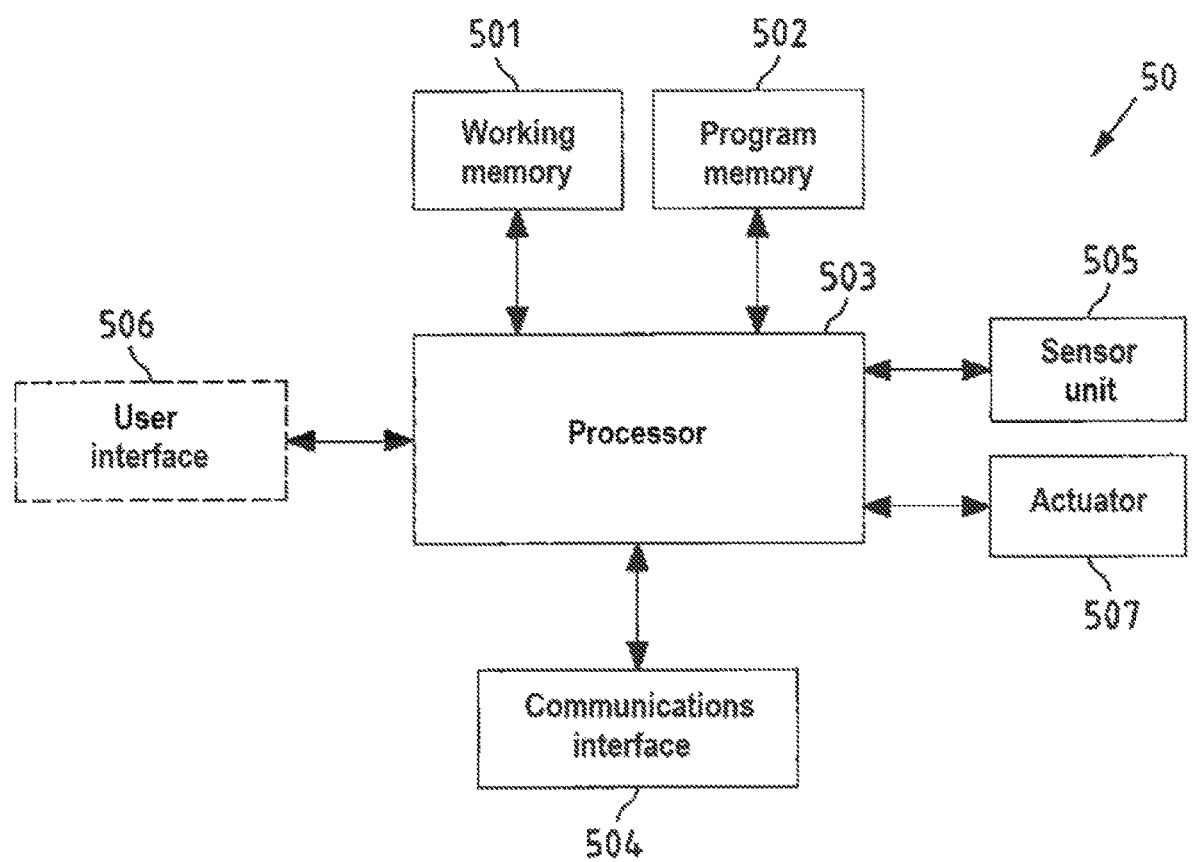
FIG. 5 shows a diagrammatic representation of an exemplary embodiment of a device in accordance with the second, third or fourth aspect.

The dosing device 1, the cleaning appliance 2, the smart phone 3, and the computing and storage device may each be represented by the device 50 of FIG. 5, for example.

Here, the dosing device 1 is disposed on a closing device of the cleaning appliance 2. Alternatively, the dosing device may be configured so as to be movable, so that the dosing device 1 may, for example, be freely positionable in the interior of the cleaning appliance 2. The dosing device 1 must, for example, be positionable with respect to a cleaning appliance 2 in a manner such that on the one hand the dosing device 1 can detect an odor load in the interior of the cleaning appliance 2, and on the other hand can initiate fragrancing and/or deodorizing in a manner such that released fragrancing and/or deodorizing agent can be distributed in the interior of the cleaning appliance 2. Otherwise, for example, an odor load in the interior of the cleaning appliance 2 could not be removed by the dosing device 1.

The dosing device 1 comprises a sensor unit 11, a control unit 12, an actuator 13 and a communication interface 14. Furthermore, the dosing device 1 comprises, for example, a cartridge for storing at least one preparation of a fragrancing and/or deodorizing agent which can be coupled to the dosing device 1.

The sensor unit 11 comprises at least one odor sensor, wherein acquisition of first information indicative of an odor load in the interior of the cleaning appliance 2 is possible therewith.

Fragrancing and/or deodorizing information may be produced using the control unit 12, wherein the fragrancing and/or deodorizing information based on the first information captured by the sensor unit 11 can be produced.

The actuator 13 is configured in a manner such that fragrancing and/or deodorizing can be initiated. The fragrancing and/or deodorizing is carried out in accordance with the fragrancing and/or deodorizing information produced by the control unit 12. At least one preparation of a fragrancing and/or deodorizing agent (for example the fragancing and/or deodorizing agent which is stored in the cartridge) can be released by the actuator 13, corresponding to the fragrancing and/or deodorizing information. An odor load in the interior of the cleaning appliance 2 can be removed by releasing the fragrancing and/or deodorizing agent.

The computing and storage device comprises a server 51 and a database 52. The server 51 and the database 52 here are separated from each other and connected together via a communication connection in order to exchange data. In an alternative embodiment, the server 51 and the database 52 are placed together in one device.

The dosing device 1, the smart phone 3, the computing and storage device and the cleaning appliance 2 are connected together via the communication network 4. Correspondingly, the dosing device 1, the smart phone 3, the computing and storage device and the cleaning appliance 2 can be either directly linked together (as indicated, for example by the dashed arrow between the dosing device 1 and the smart phone 3), for example to form a communication connection. In addition or as an alternative, the dosing device 1, the smart phone 3, the central computing and storage device and the cleaning appliance 2 may respectively together form and accordingly use communication connections to exchange data via the communication network 4. Examples of communication connections that may be used are local radio connections (for example via Bluetooth) or wireless radio connections (for example via WLAN, SubGHz with a private or public network). As an example, the dosing device 1 may form and accordingly use a communication connection with a public or private network, such as communication network 4, for example, and/or an end device, for example a PC, smart phone (for example smart phone 3) or an interactive social communication system (for example Amazon Echo). As an example, the dosing device 1 here comprises a communication interface 14 for using one of the communication connections mentioned above. The other entities (for example the cleaning appliance 2, the smart phone 3 and/or the computing and storage device) comprise a corresponding communication interface, for example.

The dosing device 1 may, for example, be integrated into the cleaning appliance 2. Alternatively, the dosing device 1 is a mobile device. When configured as a mobile device, the dosing device can be positioned essentially freely in the interior of the cleaning appliance. The dosing device 1 may operate independently, i.e. for example without connecting to the communication network 4. A message regarding the operational status of the dosing device 1 and/or additionally regarding the cleaning appliance 2 may, for example, be carried out directly at the dosing device 1, for example by employing an indicating device (for example for relaying at least one light signal, acoustic signal and/or optical signal). Optionally, the dosing device may comprise or have such an indicating device (for example a display).

The system 1 enables fragrancing, deodorizing or combined fragrancing and deodorizing of an interior of a cleaning appliance, in particular to remove an odor load prevailing in the interior of the cleaning appliance, for example in the interior of the cleaning appliance 2.

In an exemplary embodiment, first information is captured from the sensor unit 11 of the dosing device 1. This captured first information is transmitted to the server 51 of the computing and storage device via the communication network 4. Based on the captured first information, the server produces fragrancing and/or deodorizing information and transmits it to the dosing device 1 via the communication network 4. Based on the fragrancing and/or deodorizing information produced, in the dosing device 1, fragrancing and/or deodorization of the interior of the cleaning appliance 1 is initiated. The dosing device 1 may, for example, construct a communication connection to the smart phone 3, for example after a successful request to construct the communication connection which the dosing device 1 has obtained from the smart phone 3. Information in particular regarding the olfactory status of the interior of the cleaning appliance 2 may be transmitted to the user of the smart phone 3 via the communication connection formed, for example as to whether an unpleasant odor load that could from time to time be perceived by the user as unpleasant is or is not present in the interior of the cleaning appliance 2. As an example, a simple description such as "bad odor detected" could be transmitted to the smart phone 3. In addition, more complex status information such as, for example "Smell of sour milk or vinegar in the dishwasher" could be transmitted to the smart phone 3. Next, for example, the user could initiate fragrancing and/or deodorization of the interior of the cleaning appliance 2. In this regard, for example, fragrancing and/or deodorizing information which in this case is produced by the smart phone 3, could be transmitted to the dosing device 1. Alternatively or in addition, the dosing device 1 could (in particular) automatically initiate fragrancing and/or deodorizing.

Figure 2:
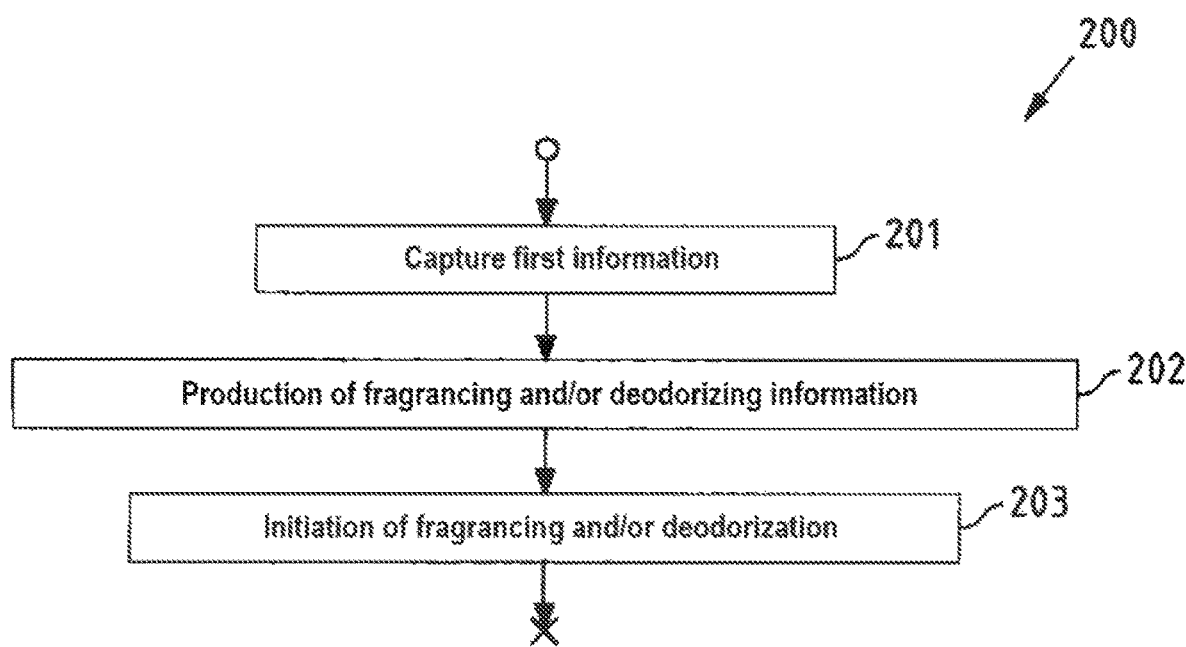
FIG. 2 shows a flow diagram of an exemplary embodiment of a method in accordance with the first aspect.

FIG. 2 shows a flow diagram 200 of an exemplary embodiment of a method which can be carried out in the context of the described aspects. The method is, for example, carried out by the control unit 12 of the dosing device 1 of FIG. 1 which, for example, may be configured as the device 50 of FIG. 5.

In a first step 201, first information is captured. The first information is indicative of an odor load in the interior of the cleaning appliance, wherein the first information is captured with at least one odor sensor. The odor sensor is, for example, formed by the sensor unit 11 of the dosing device 1 of FIG. 1.

In a second step 202, fragrancing and/or deodorizing information is produced. Production is at least partially based on the first information captured in step 201.

In a third step 203, fragrancing and/or deodorization is initiated. Initiation of fragrancing and/or deodorization is carried out by employing an actuator (for example actuator 13 of the dosing device 1 of FIG. 1). The actuator is configured to release fragrancing and/or deodorizing agent based on the fragrancing and/or deodorizing information.

The flow diagram 200 may be executed at regular time intervals. This can ensure that a treatment or measure for removing an odor load which is present is carried out. By executing the flow diagram 200 several times, then, a tailored removal of the odor load can be carried out either by fragrancing or by deodorization or by a combination of fragrancing and deodorization.

Figure 3:
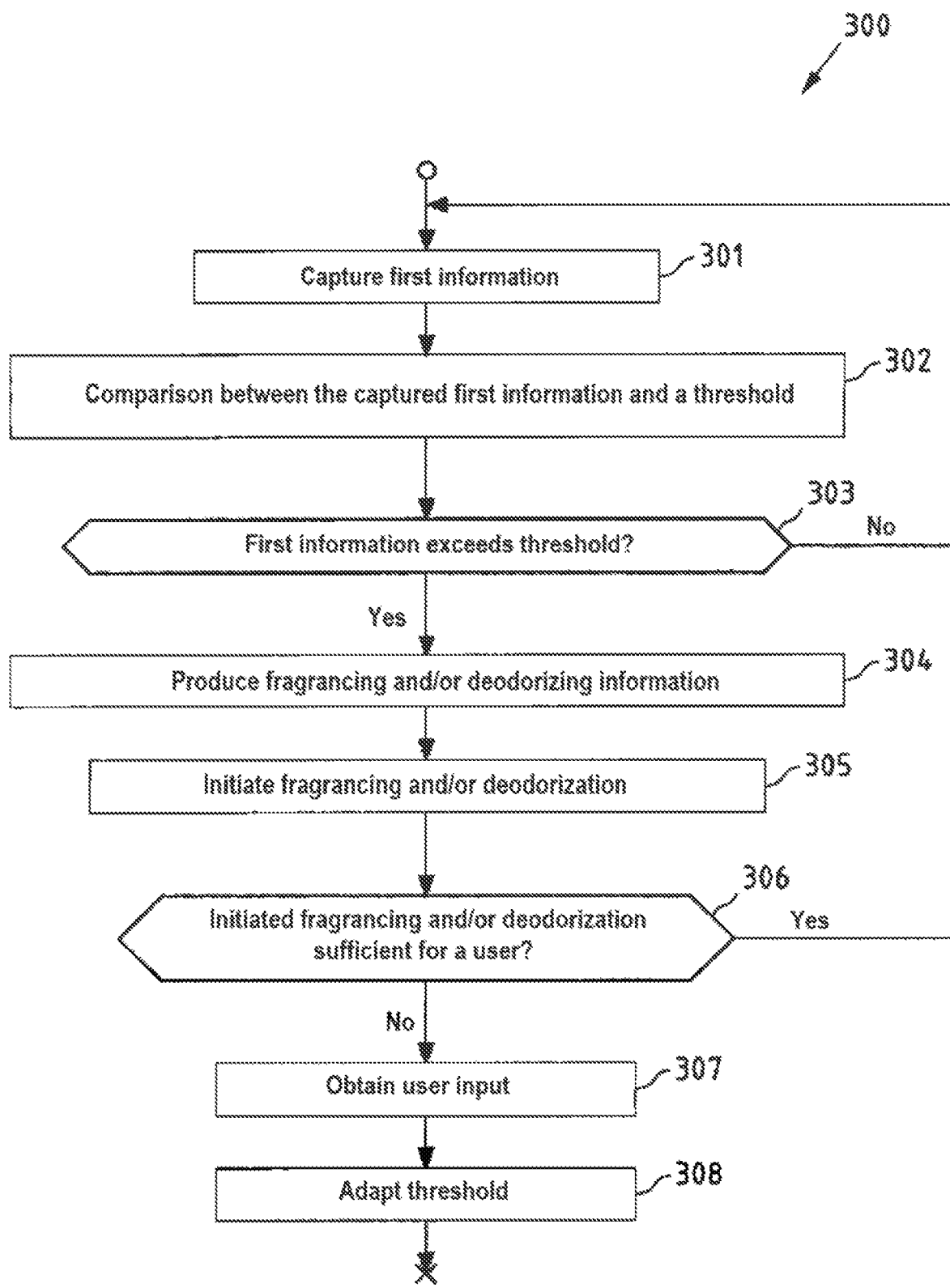
FIG. 3 shows a flow diagram of an exemplary embodiment of a method in accordance with the first aspect.

FIG. 3 shows a flow diagram 300 for an exemplary embodiment of a method which can be carried out in the context of the described aspects. The method is carried out, for example, by the control unit 12 of the dosing device 1 of FIG. 1 which, for example, may be configured as device 50 in FIG. 5.

In a first step 301, first information is captured. The first information is indicative of an odor load in the interior of a cleaning appliance, wherein the first information is captured with at least one odor sensor. The odor sensor is formed, for example, by the sensor unit 11 of the dosing device 1 of FIG. 1.

In a second step 302, a comparison between the captured first information and a predefined threshold is carried out. The captured first information and/or the predefined threshold are, for example, indicative of at least one of the following parameters:

intensity of the odor load in the interior of the cleaning appliance;
  type of odor load in the interior of the cleaning appliance;
  dynamics of the odor load in the interior of the cleaning appliance;
  or a combination thereof.

In a third step 303, checks as to whether the captured first information exceeds the threshold are carried out. In the case in which the captured first information does not exceed the threshold, the odor load prevailing in the interior of the cleaning appliance is not yet so strong that it would be perceived by a user as disruptive or unpleasant. This might be the case, for example, when the odor load is still very low or when the cleaning appliance has just been emptied or cleaned. For the other case in which the captured first information exceeds the predefined threshold, then in step 304, fragrancing and/or deodorizing information is produced. The fragrancing and/or deodorizing information in this case is indicative of an odor load in the interior of the cleaning appliance which the user could from time to time perceive as disruptive or unpleasant.

In an alternative embodiment of the flow diagram 300, step 304, in which fragrancing and/or deodorizing information is produced, may be carried out before the step 303 so that—independently of the comparative results of step 302—fragrancing and/or deodorizing information is always produced. The fragrancing and/or deodorizing information produced is, for example, indicative of an odor load in the interior of the cleaning appliance which is perceived by a user as unpleasant or indicative of an odor load in the interior of the cleaning appliance which is not perceived by the user as unpleasant. Next, a check can be carried out as to whether the captured first information exceeds the predefined threshold, so that a decision can be made as to whether or not to initiate fragrancing and/or deodorization to remove an occasional unpleasant odor load in the interior of the cleaning appliance.

Based on the fragrancing and/or deodorizing information produced in step 304, in step 305, fragrancing and/or deodorizing is initiated. As an example, initiation of fragrancing and/or deodorization is carried out when the fragrancing and/or deodorizing information produced is indicative of an odor load in the interior of the cleaning appliance which is perceived by a user as unpleasant. Initiation of fragrancing and/or deodorization may, for example, release different fragrancing and/or deodorizing agents depending on the type of odor load in the interior of the cleaning appliance. Alternatively or in addition, initiation of fragrancing and/or deodorization may release different quantities of a fragrancing and/or deodorizing agent, for example as a function of the intensity of the odor load in the interior of the cleaning appliance.

In step 306, a check is carried out as to whether the initiated fragrancing and/or deodorizing was sufficient for the user or not, for example whether an odor load in the interior of the cleaning appliance perceived by the user as unpleasant has or has not been removed by the initiated fragrancing and/or deodorizing. The aim of this check may, for example, be to question the user as to whether the treatment of the odor load in the interior of the cleaning appliance by the initiated fragrancing and/or deodorizing, was sufficient (for example whether the intensity of the odor load in the interior of the cleaning appliance has been sufficiently reduced), whether it was pleasant (for example in the context of hedonics, whether the odor of the released fragrancing and/or deodorizing agent itself was pleasant for the user), and/or whether the initiated fragrancing and/or deodorizing should perhaps be repeated (for example with a different intensity and/or quantity of released fragrancing and/or deodorizing agent). If the initiated fragrancing and/or deodorizing was sufficient for the user, then the flow diagram 300 can be executed again. Otherwise, for example, continue to step 307.

In step 307, a user input is obtained. The user input may, for example, be based on a question transmitted to the user. The user input may, for example represent whether the treatment of the odor load in the interior of the cleaning appliance by the initiated fragrancing and/or deodorizing was sufficient, whether it was pleasant, whether the initiated fragrancing and/or deodorizing should perhaps be repeated, or a combination thereof. Alternatively, the user input can be captured in step 307.

Capturing the user input comprises, for example, machine acquisition of information, for example an input on an input device which is executed by the user, for example using by keying in on a keypad and/or on a touch-sensitive display device. The user input may, for example, be captured using means for capturing the user input which, for example, are part of the device (for example device 50 of FIG. 5) or of the system (for example system 1 of FIG. 1). If the user input is obtained such as, for example in step 307, the user input that is obtained is captured as described above.

In step 308, the predefined threshold is adapted. The predefined threshold is adapted, for example, based on the user input which is received or captured. The predefined threshold that is consulted for checking may be adapted (for example varied) in correspondence with the obtained or captured user input. Adapting the predefined threshold means that, for example when the flow diagram 300 is next executed, the comparison carried out in step 302 could lead to a result other than when the comparison with the predefined threshold was carried out in step 302 which was not adapted in correspondence with the obtained or captured user input (step 307). If the obtained or captured user input is, for example, indicative of the fact that despite the initiated fragrancing and/or deodorization, the removal of the odor load in the interior of the cleaning appliance is perceived as not sufficient, then adapting the predefined threshold could decrease this threshold. Correspondingly, for example, an increased quantity of fragrancing and/or deodorizing agent may be released in the context of initiating fragrancing and/or deodorization, or vice versa.

Figure 4:
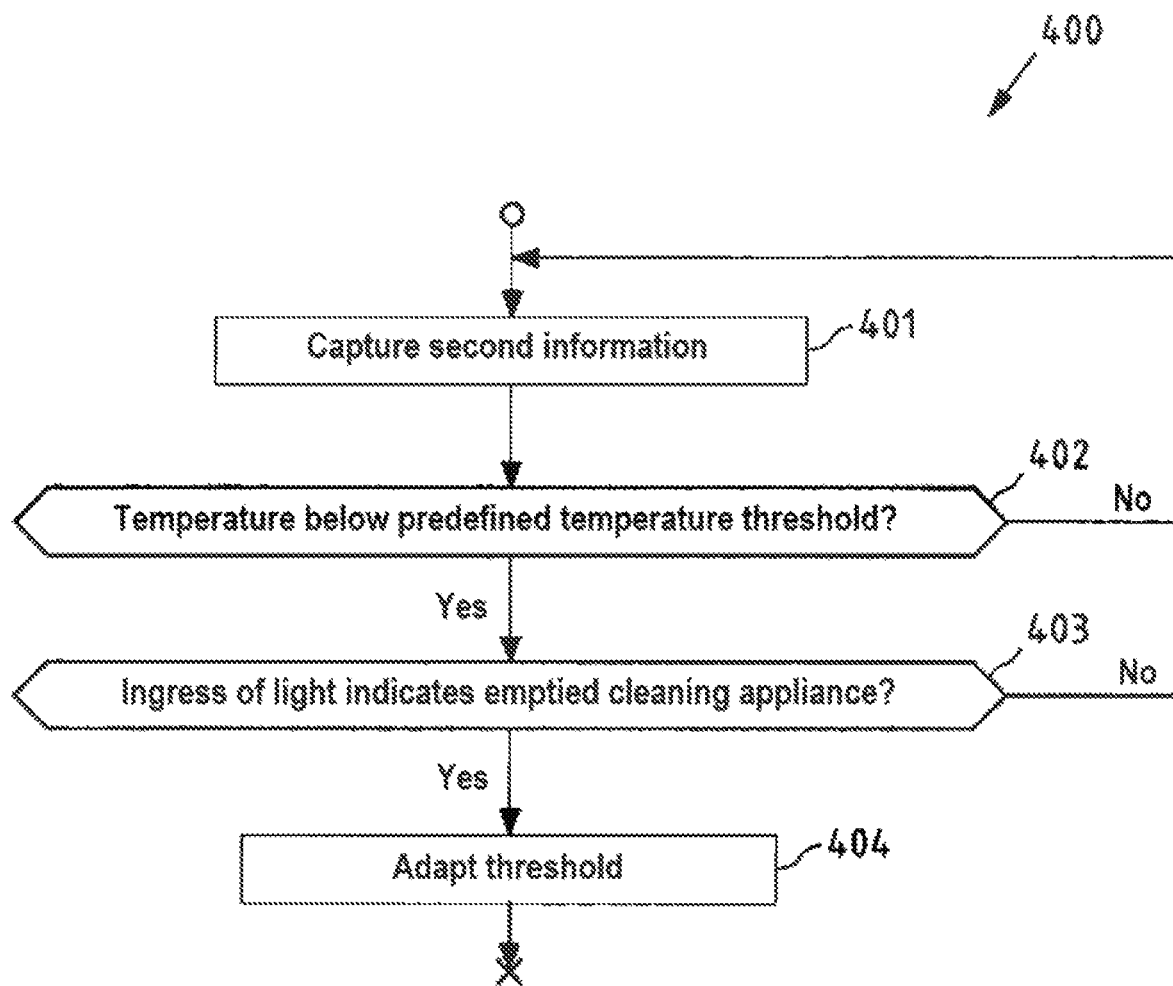
FIG. 4 shows a flow diagram of a partial aspect of an exemplary embodiment of a method in accordance with the first aspect.

FIG. 4 shows a flow diagram 400 for an exemplary embodiment of a method which can be carried out in the context of the described aspects. The method is carried out, for example, by the control unit 12 of the dosing device 1 of FIG. 1 which, for example, may be configured as the device 50 of FIG. 5.

As an example, the flow diagram 400 will be executed in the context of the "calibration" of the control unit 12 of the dosing device 1 of FIG. 1. So that the acquisition of first information indicative of an odor load in the interior of the cleaning appliance functions reliably, regular calibration must be carried out, for example. During calibration, for example, the predefined threshold for comparison with the captured first information is set. By way of example, zero-point calibration is described below. The zero-point calibration may, for example, be carried out in the empty or clean condition of the cleaning appliance and can in particular be started or triggered upon detecting the empty or clean condition of the cleaning appliance, for example by a corresponding control signal from the processor.

In step 401, second information is captured. Second information here is indicative of an ingress of light and a temperature in the interior of the cleaning appliance, wherein the second information is captured by at least one light sensor and at least one temperature sensor.

In order to detect whether the cleaning appliance is in the empty or clean condition, in step 402, a check is carried out as to whether the temperature in the interior of the cleaning appliance is below a predefined temperature threshold. Because a raised temperature regularly prevails in the interior of the cleaning appliance when carrying out the cleaning cycle, then in the case in which the temperature according to the captured second information is above the predefined temperature threshold, then the cleaning appliance is not in the empty or clean condition. Correspondingly, the flow diagram 400 can be executed again so that, for example at a later point in time, a check can be carried out as to whether the temperature in the interior of the cleaning appliance is below the predefined temperature threshold.

In the case in which the temperature is below the predefined threshold, in step 403, a check is carried out as to whether the ingress of light has been detected by the at least one light sensor. By employing the ingress of light in combination with a temperature drop, which can be detected via the at least one temperature sensor, the ingress of light can indicate that emptying (for example of crockery) of the cleaning appliance has taken place. In the case in which the ingress of light detected by the at least one light sensor indicates that the cleaning appliance has not been emptied, then correspondingly, the cleaning appliance is not in the empty or clean condition. Correspondingly, the flow diagram 400 can be executed again so that this can be checked at a later point in time, for example.

When the temperature in the interior of the cleaning appliance has fallen below a specific temperature threshold and the cleaning appliance has been emptied, in step 404, the threshold is adapted (not the temperature threshold), so that a zero-point calibration is carried out. In this regard, the first information captured from the at least one odor sensor (for example absolute measured values captured from the at least one odor sensor) is stored. This stored first information acts, for example, to monitor the ageing of the at least one odor sensor. The evaluation of this stored first information may be used, for example, in order to inform a user of the cleaning appliance when the sensitivity of the at least one odor sensor diminishes, and it should perhaps be replaced in order to ensure orderly function of the (in particular automatic) fragrancing and/or deodorizing.

The first information captured by the at least one odor sensor (for example absolute measured values from the at least one odor sensor) which is stored in the empty or clean state of the cleaning appliance, exemplify a status of the interior of the cleaning appliance which is almost free from disruptive odors, i.e. a neutral odor load in the interior of the cleaning appliance. In order to check whether a neutral odor load is present in the interior of the cleaning appliance, initiation of the release of a defined quantity of fragrancing and/or deodorizing agent may be carried out, for example. In this regard, it must be ensured that at least one of the released fragrancing and/or deodorizing agents leads to a full signal deflection (100%) of the at least one odor sensor, but not to oversaturation thereof. In the case in which the at least one odor sensor is configured as an ethanol sensor then, for example, ethanol or a comparably reacting alcohol may be released as the fragrancing and/or deodorizing agent. If this is not possible, then alternatively, for example, a calibration substance or a corresponding mixture which is stored separately (for example in the dosing device) may be used or alternatively, this may be supplied from outside.

If no full signal deflection (100%) of the at least one odor sensor is detected, then a corresponding adaptation of the threshold may be undertaken so that despite compromised function of the at least one odor sensor, for example due to ageing, an odor load in the interior of the cleaning appliance can still be captured using the at least one odor sensor.

FIG. 5 shows a diagrammatic representation of an exemplary embodiment of a device 50 which can be used in the context of all aspects.

The device 50 may, for example, represent the sensor unit 11 of the dosing device 1 or the control unit 12 of the dosing device 1 of FIG. 1. The device 50 may represent the dosing device 1 of FIG. 1, for example.

The device 50 may, for example, execute the flow diagram 200 of FIG. 2, the flow diagram 300 of FIG. 3 or the flow diagram 400 of FIG. 4.

The device 50 comprises a processor 503 with associated working memory 501 and program memory 502. The processor 503 executes program instructions, for example, which are stored in the program memory 502. The program instructions execute the method in accordance with the first aspect and/or control it. In this regard, the program memory 502 contains a computer program in accordance with the fifth aspect and constitutes a computer program product for storage thereof. Device 50 constitutes an example of a device in accordance with the second aspect or a device of a system in accordance with the third aspect.

The program memory 502 may, for example, be a persistent memory such as, for example, a read only memory (ROM) memory. The program memory 502 may, for example, be firmly attached to the processor 503, but alternatively may also be detachably connected to the processor 503, for example as a memory card, diskette, or optical data carrier medium (for example a CD or DVD). Other information may also be stored in the program memory 502, or in a separate memory.

The working memory 501 is used to store temporary results during execution of the program instructions, for example; it may, for example, be a volatile memory such as, for example, a random-access memory (RAM).

Furthermore, the processor 503 is operatively connected to a communication interface 504 with which, for example, an exchange of information is possible with other devices (see, for example, the dashed arrow in FIG. 1).

The device 50 may contain other components. In the event that the device 50 represents the dosing device 1 of FIG. 1, a sensor unit 505 is provided in particular which, for example, is configured for detecting an odor load in the interior of a cleaning appliance of the first information and which is operatively connected to the processor 503. Furthermore, in particular, an actuator 507 is provided which, for example, is configured to initiate fragrancing and/or deodorization of fragrancing and/or deodorizing agents and is operatively connected to the processor 503.

Optionally, the device 50 may comprise a user interface 506 by features of which, for example, it is possible to relay information (for example optically). As an example, the user interface could be a display device (for example a liquid crystal display (LCD) or a light emitting diode (LED) display or the like).

Figure 6:
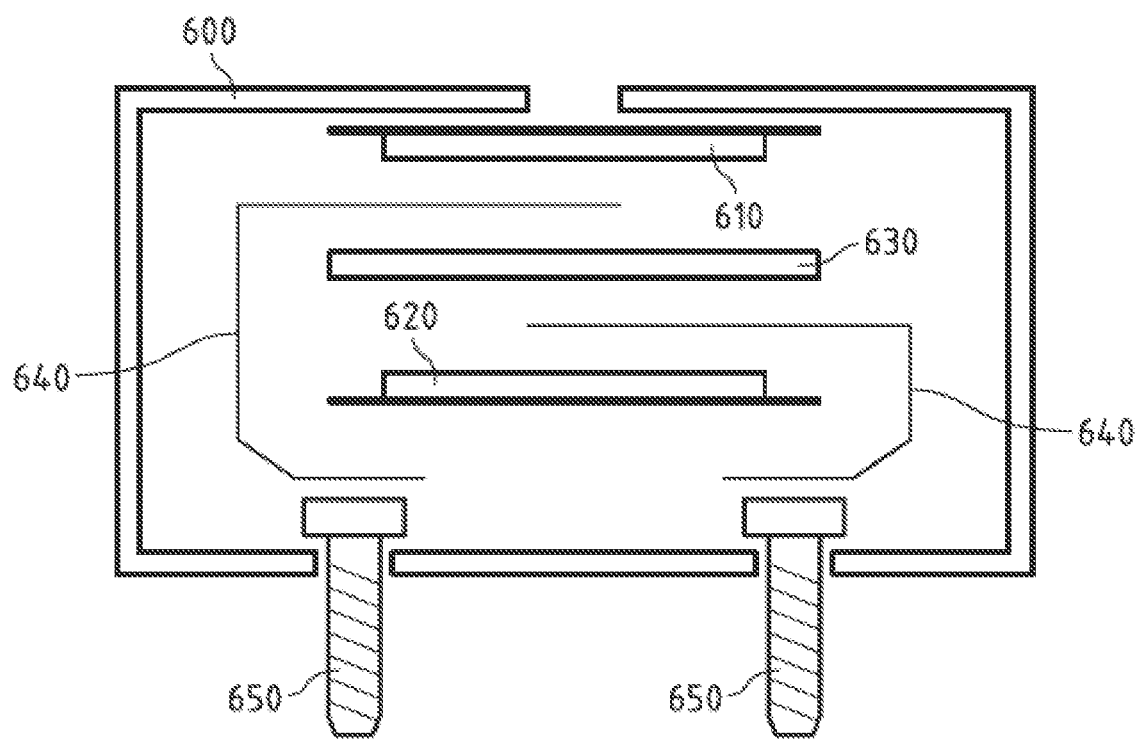
FIG. 6 shows a diagrammatic representation of a construction of an odor sensor.

FIG. 6 shows a diagrammatic (sectional) representation of the construction of an odor sensor, here an electrochemical sensor with the designation "SpecSensors 3SP Ethanol 1000 Package 110-202". By employing the odor sensor shown, ethanol can specifically be discerned (for example detected).

The odor sensor 600 comprises a measuring electrode 610 and a counter-electrode 620 which are separated from each other by a separator 630. A current collector 640 at least partially surrounds the respective electrodes 610, 620. The respective current collectors 640 are at a distance from the respective electrodes (measuring electrode 610 and counter-electrode 620). The odor sensor 600 also comprises two sensor pins 650.

FIGS. 7a-f show exemplary graphs of (first) information captured from an odor sensor. Here, exemplary electrical signals can be seen in FIGS. 7a-f which have been produced from an odor sensor configured as an ethanol sensor.

About 789 mg, about 78.9 mg and about 7.9 mg of ethanol were respectively introduced into the interior of a dishwasher. Here, the dishwasher had a treatment volume of about 183.6 L. The ethanol was introduced into the interior using a pipette. Corresponding to the vapor pressures, maximum concentrations of about 4300 ppm (very high EtOH), about 430 ppm (high EtOH) or about 43 ppm (low EtOH) were obtained in the gas phase. An odor sensor is located in the dishwasher, here an electrochemical sensor of the "SpecSensors 3SP Ethanol 1000 Package 110-202" type, disposed in order to detect the introduced ethanol.

Figure 7A:
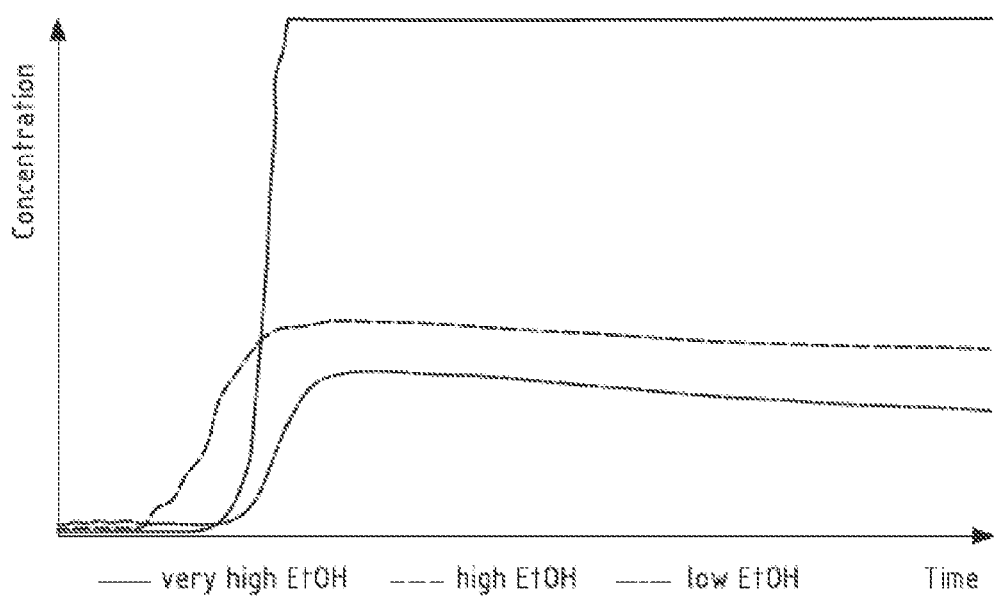
FIGS. 7a-f show exemplary graphs of information captured by an odor sensor.

FIG. 7a shows the electrode signal captured from an odor sensor, here an ethanol sensor as described in this specification. Here, the various captured ethanol concentrations are shown over a period of time. The acquisition of the ethanol concentrations was carried out in a closed dishwasher which was not ventilated. The respective graphs show that even very small concentrations (low EtOH=43 ppm), as occur with biological decomposition processes, could be detected using the ethanol sensor. Surprisingly, it was discovered that even complex alcohol molecules were detectable using an ethanol sensor.

Figure 7B:
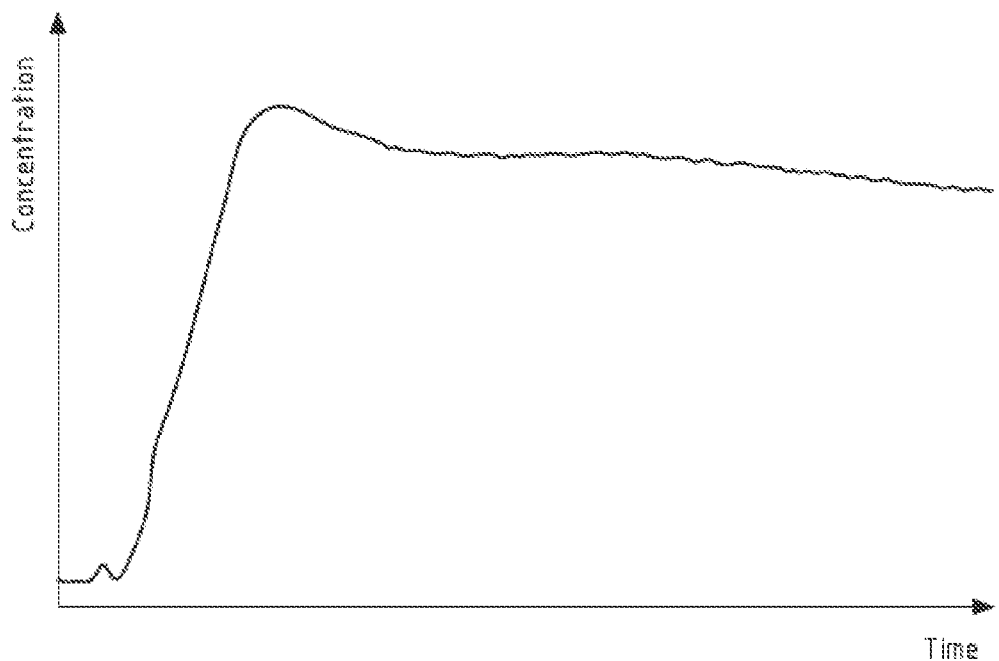

FIG. 7b shows an exemplary graph of (first) information captured from an odor sensor, which here represents an isopropanol concentration.

The graph shown in FIG. 7h shows the concentration-time profile of a dose of about 39 mg of 2-propanol in a closed dishwasher which was not ventilated, corresponding to a concentration of about 212 ppm. The sensor response to this detected concentration (detected as an electrical signal) can clearly be seen.

Figure 7C:
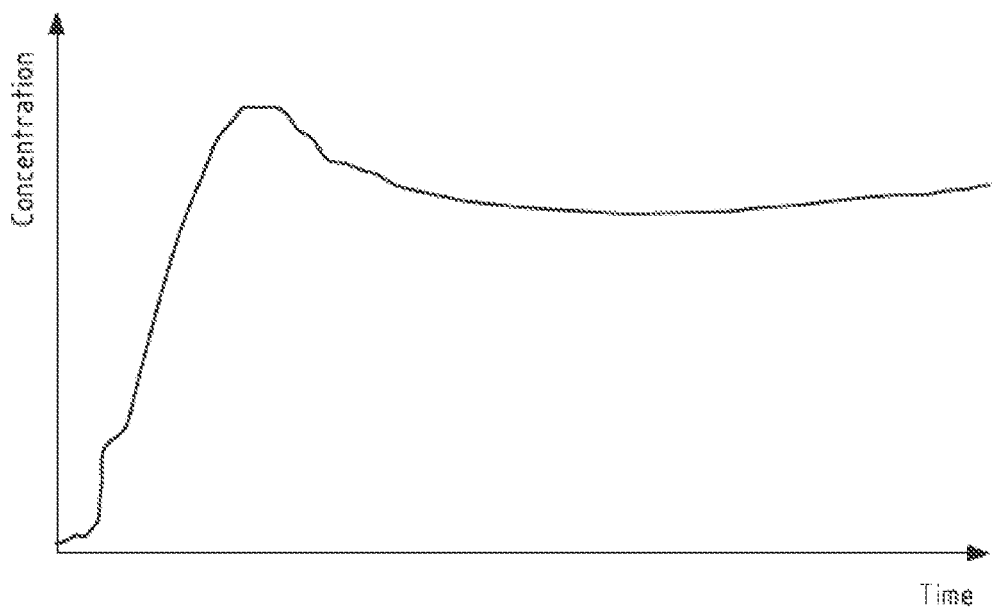

FIG. 7c shows an exemplary graph of (first) information captured from an odor sensor, which here represents a concentration of 1-butanol.

The graph shown in FIG. 7c shows the concentration-time profile of a dose of about 40.5 mg of 1-butanol in a closed dishwasher which was not ventilated, corresponding to a concentration of about 220 ppm. The sensor response to this detected concentration (detected as an electrical signal) can clearly be seen.

Figure 7D:
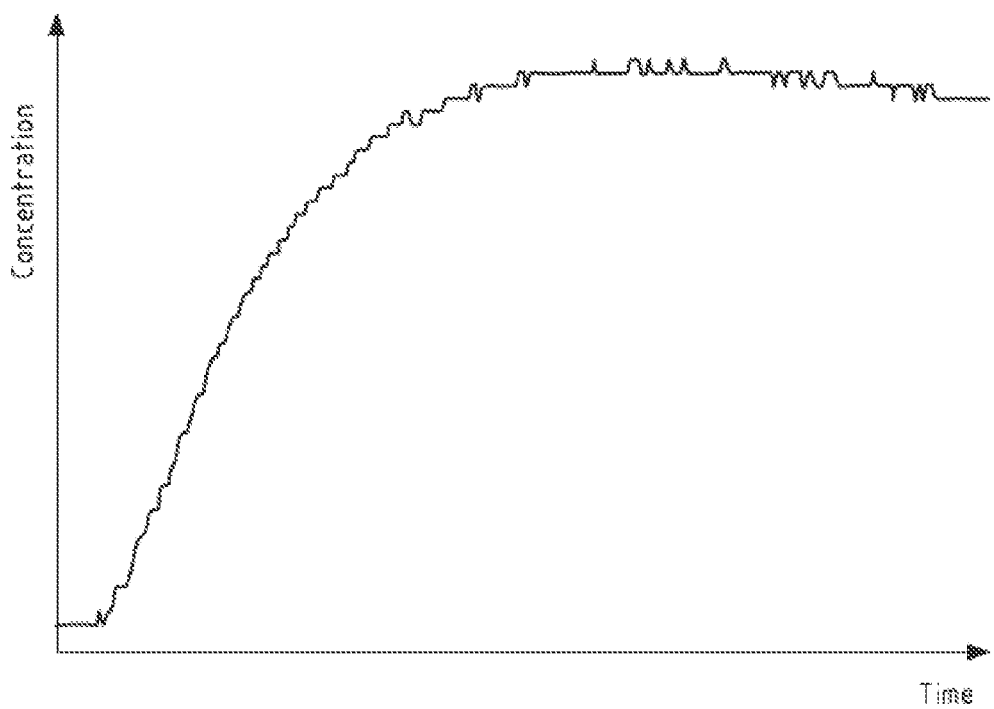

FIG. 7d shows an exemplary graph of (first) information captured from an odor sensor, which here represents a concentration of ethyl acetate.

The graph shown in FIG. 7d shows the concentration-time profile of a dose of about 44.7 mg of ethyl acetate in a closed dishwasher which was not ventilated, corresponding to a concentration of about 243 ppm. The sensor response to this detected concentration (detected as an electrical signal) can clearly be seen.

Figure 7E:
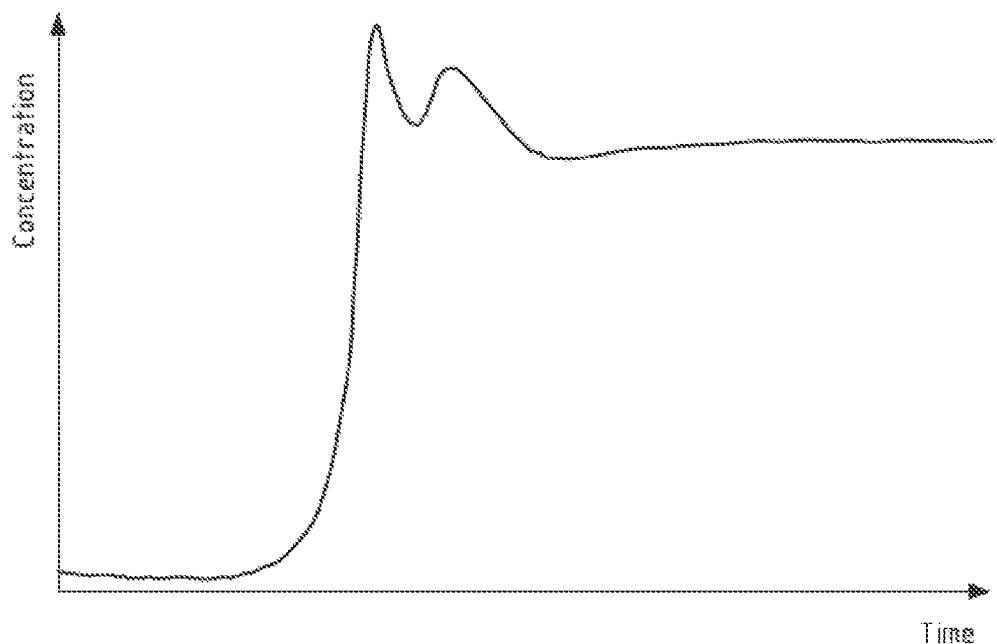

FIG. 7e shows an exemplary graph of (first) information captured from an odor sensor, which here represents a concentration of i-butyraldehyde.

The graph shown in FIG. 7e shows the concentration-time profile of a dose of about 39.5 mg of i-butyraldehyde in a closed dishwasher which was not ventilated, corresponding to a concentration of about 215 ppm. The sensor response to this detected concentration (detected as an electrical signal) can clearly be seen.

Figure 7F:
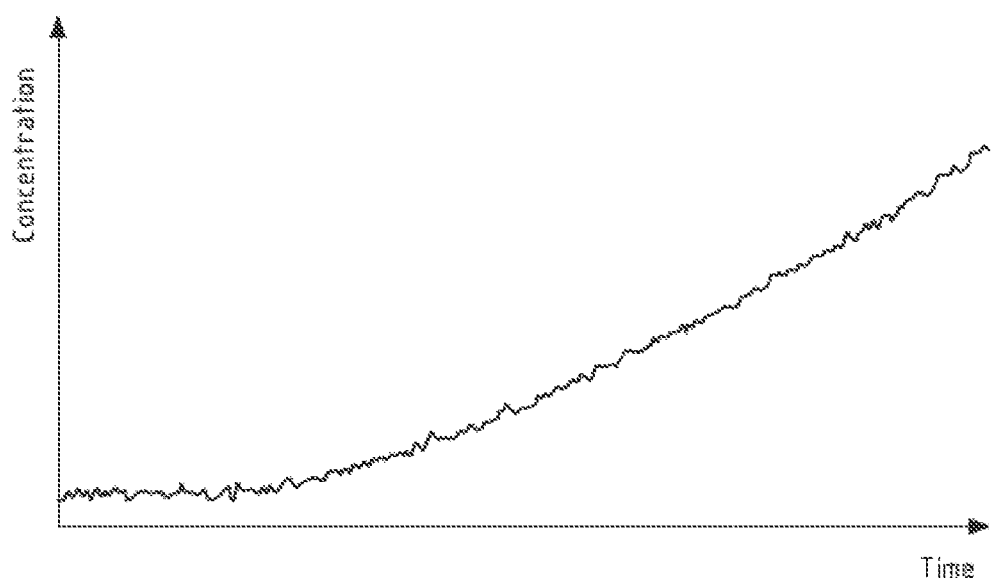

FIG. 7f shows an exemplary graph of (first) information captured from an odor sensor, which here represents a concentration of 2-propanone (acetone).

The graph shown in FIG. 7f shows the concentration-time profile of a dose of about 395 mg of 2-propanone (acetone) in a closed dishwasher which was not ventilated, corresponding to a concentration of about 2151 ppm. The sensor response to this detected concentration (detected as an electrical signal) can be seen, but is weak compared with the graphs of FIGS. 7b-e.

The exemplary embodiments described in this specification and the associated respective optional features and properties described should also be understood to have been disclosed in any combinations thereof. In particular, in addition, the description of a feature comprised in one exemplary embodiment—unless explicitly stated otherwise—should not be construed here to mean that the feature is essential or vital to the function of the exemplary embodiment. The sequence of the steps of the method described in this specification in the individual flow diagrams is not mandatory; alternative sequences for the steps of the method may be envisaged. The steps of the method may be implemented in various manners, and so an implementation in software (through program instructions), hardware or a combination of the two may be envisaged for the purposes of implementing the steps of the method.

Terms such as "comprise", "provided with", "contained", "contain" and the like in the patent claims do not exclude other elements or steps. The formulation "at least partially" includes both the "partially" and also the "completely" cases. The formulation "and/or" should be understood to mean that both the alternatives and also the combination thereof are disclosed, and so "A and/or B" means "(A) or (B) or (A and B)". The use of the indefinite article does not exclude a plurality. An individual device may carry out the functions of several units or devices cited in the patent claims. Reference numerals given in the patent claims should not be considered to be limitations upon the corresponding means and steps.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method carried out by one or more devices, comprising:
   capturing first information or obtaining captured first information indicative of an odor load in the interior of a cleaning appliance, wherein the first information is captured from at least one odor sensor;
   producing fragrancing and/or deodorizing information based at least in part on the captured or obtained first information or outputting the captured first information in order to produce the fragrancing and/or deodorizing information, wherein the production of the fragrancing and/or deodorizing information comprises a comparison between the captured or obtained first information and a predefined threshold;
   initiating fragrancing and/or deodorization by at least one actuator for releasing a fragrancing and/or deodorizing agent based on the fragrancing and/or deodorizing information produced;
   obtaining a user input concerning an adjustment of the predefined threshold; and
   adapting the predefined threshold based on the obtained user input.

2. The method as claimed in claim 1, wherein the captured or obtained first information and/or the predefined threshold are indicative of at least one of the following parameters:
   an intensity of the odor load in the interior of the cleaning appliance;
   a type of the odor load in the interior of the cleaning appliance;
   dynamics of the odor load in the interior of the cleaning appliance;
   or a combination thereof.

3. The method as claimed in claim 1, the method further comprising:
   capturing second information or obtaining captured second information indicative of an ingress of light and/or a temperature in the interior of the cleaning appliance, wherein the second information is captured by at least one light sensor and/or at least one temperature sensor.

4. The method as claimed in claim 3, the method further comprising:
   adapting the predefined threshold based on the captured second information.

5. The method as claimed in claim 3, wherein the at least one odor sensor and the at least one light sensor and/or the at least one temperature sensor form a sensor array.

6. The method as claimed in claim 1, wherein the method is carried out and/or controlled between two cleaning cycles of the cleaning appliance.

7. The method as claimed in claim 1, wherein initiation of the fragrancing and/or deodorization releases different fragrancing and/or deodorizing agents.

8. The method as claimed in claim 1, wherein initiation of the fragrancing and/or deodorization releases different quantities of the fragrancing and/or deodorizing agent.

9. The method as claimed in claim 3, wherein the method further comprises:
   adapting the predefined threshold by a zero point calibration when the temperature has dropped below a predefined temperature threshold and the ingress of light has signaled emptying of the cleaning appliance.

10. The method as claimed in claim 7, wherein the initiation of the fragrancing and/or deodorization releases the different fragrancing and/or deodorizing agents as a function of a type of the odor load in the interior of the cleaning appliance.

11. The method as claimed in claim 8, wherein the initiation of the fragrancing and/or deodorization releases the different quantities of the fragrancing and/or deodorizing agent as a function of an intensity of the odor load in the interior of the cleaning appliance.

12. A method carried out by one or more devices, comprising:
    capturing first information or obtaining captured first information indicative of an odor load in the interior of a cleaning appliance, wherein the first information is captured from at least one odor sensor;
    producing fragrancing and/or deodorizing information based at least in part on the captured or obtained first information or outputting the captured first information in order to produce the fragrancing and/or deodorizing information, wherein the production of the fragrancing and/or deodorizing information comprises a comparison between the captured or obtained first information and a predefined threshold;
    initiating fragrancing and/or deodorization by at least one actuator for releasing a fragrancing and/or deodorizing agent based on the fragrancing and/or deodorizing information produced;
    capturing second information or obtaining captured second information indicative of an ingress of light and/or a temperature in the interior of the cleaning appliance, wherein the second information is captured by at least one light sensor and/or at least one temperature sensor; and adapting the predefined threshold by a zero point calibration when the temperature has dropped below a predefined temperature threshold and the ingress of light has signaled emptying of the cleaning appliance.

\* \* \* \* \*